(12) United States Patent
Konrad, Jr. et al.

(10) Patent No.: US 10,888,694 B2
(45) Date of Patent: Jan. 12, 2021

(54) COMPOUNDING DEVICE, SYSTEM, KIT, SOFTWARE, AND METHOD

(71) Applicant: B. Braun Medical Inc., Bethlehem, PA (US)

(72) Inventors: Karl Konrad, Jr., Bethlehem, PA (US); Mike Janders, Bethlehem, PA (US); Aaron S. Pearl, Baltimore, MD (US)

(73) Assignee: B. Braun Medical Inc., Bethlehem, PA (US)

( * ) Notice: Subject to any disclaimer, the term of this patent is extended or adjusted under 35 U.S.C. 154(b) by 11 days.

(21) Appl. No.: 16/408,440

(22) Filed: May 9, 2019

(65) Prior Publication Data

US 2019/0262790 A1    Aug. 29, 2019

Related U.S. Application Data

(63) Continuation of application No. 15/490,372, filed on Apr. 18, 2017, now Pat. No. 10,315,174, which is a
(Continued)

(51) Int. Cl.
*A61M 39/22* (2006.01)
*F16K 5/04* (2006.01)
(Continued)

(52) U.S. Cl.
CPC .......... *A61M 39/223* (2013.01); *A61J 3/002* (2013.01); *A61M 39/24* (2013.01); *B01F 3/0861* (2013.01);
(Continued)

(58) Field of Classification Search
CPC ........ F16K 5/02; F16K 5/0207; F16K 5/0214; F16K 11/083; F16K 11/085;
(Continued)

(56) References Cited

U.S. PATENT DOCUMENTS 260,972 A * 7/1882 Goodrich .............. F16K 5/0414
251/310
374,978 A 12/1887 Lathrop
(Continued)

FOREIGN PATENT DOCUMENTS

| WO | 03/058507 A1 | 7/2003 |
|----|--------------|--------|
| WO | 2013/043868 A1 | 3/2013 |
| WO | 2017/011398 A1 | 1/2017 |

OTHER PUBLICATIONS

Australian Examination Report No. 1 for the related Australian Patent Application No. 2016291707 dated Mar. 18, 2020.

*Primary Examiner* — Seth W. Mackay-Smith
(74) *Attorney, Agent, or Firm* — Kenealy Vaidya LLP

(57) ABSTRACT

An exemplary pharmaceutical compounding system and device for mixing materials from at least two distinct material sources can include a valve including a valve housing and a valve structure located within the valve housing. The valve structure can be configured to permit fluid to flow through the valve when in an open position, and can include a gravity wall wherein, when the valve structure is in the open position, fluid moving through the valve structure moves upward against a force of gravity when travelling through the valve and traversing the gravity wall.

18 Claims, 33 Drawing Sheets

Related U.S. Application Data continuation of application No. 14/797,000, filed on Jul. 10, 2015, now Pat. No. 9,623,389, which is a continuation of application No. 14/731,042, filed on Jun. 4, 2015, now Pat. No. 9,802,172, which is a continuation of application No. 14/719,936, filed on May 22, 2015, now Pat. No. 10,143,985, which is a continuation of application No. 14/700,779, filed on Apr. 30, 2015, now Pat. No. 9,802,171, which is a continuation of application No. 14/693,867, filed on Apr. 23, 2015.

(51) Int. Cl.

| | | |
|---|---|---|
| *F16K 11/22* | (2006.01) | |
| *A61J 3/00* | (2006.01) | |
| *B65B 3/12* | (2006.01) | |
| *F16K 31/04* | (2006.01) | |
| *F16K 11/085* | (2006.01) | |
| *B01F 13/10* | (2006.01) | |
| *B01F 15/02* | (2006.01) | |
| *B01F 3/08* | (2006.01) | |
| *B01F 5/04* | (2006.01) | |
| *B01F 13/00* | (2006.01) | |
| *B01F 5/00* | (2006.01) | |
| *A61M 39/24* | (2006.01) | |
| *F16K 99/00* | (2006.01) | |

(52) U.S. Cl.
CPC ............ *B01F 3/0865* (2013.01); *B01F 5/008* (2013.01); *B01F 5/04* (2013.01); *B01F 5/0403* (2013.01); *B01F 13/0059* (2013.01); *B01F 13/0064* (2013.01); *B01F 13/1055* (2013.01); *B01F 13/1066* (2013.01); *B01F 15/026* (2013.01); *B01F 15/0243* (2013.01); *B01F 15/0245* (2013.01); *B65B 3/12* (2013.01); *F16K 5/04* (2013.01); *F16K 5/0407* (2013.01); *F16K 5/0414* (2013.01); *F16K 11/085* (2013.01); *F16K 11/22* (2013.01); *F16K 31/041* (2013.01); *F16K 99/0013* (2013.01); *F16K 99/0042* (2013.01); *A61J 2200/70* (2013.01); *A61M 2039/229* (2013.01); *B01F 2215/0014* (2013.01); *B01F 2215/0032* (2013.01); *B01F 2215/0034* (2013.01); *B01F 2215/0036* (2013.01); *F16K 11/0856* (2013.01); *F16K 2099/0084* (2013.01)

(58) Field of Classification Search
CPC .. F16K 5/0407; F16K 5/0414; A61M 39/223; A61M 2039/229
See application file for complete search history.

(56) References Cited

U.S. PATENT DOCUMENTS

| | | | |
|---|---|---|---|
| 463,138 A | 11/1891 | Carroll | |
| 784,849 A | 3/1905 | Fuqua | |
| 901,621 A * | 10/1908 | Jones | F16K 5/162 |
| | | | 251/161 |
| 973,819 A * | 10/1910 | Schmaal et al. | F16K 5/0414 |
| | | | 251/310 |
| 1,043,935 A | 11/1912 | Hitchcock | |
| 1,061,825 A | 5/1913 | Dewey | |
| 1,403,396 A | 1/1922 | Erickson | |
| 2,702,050 A | 2/1955 | Thomas | |
| 3,038,694 A * | 6/1962 | Dunbeck | F16K 27/062 |
| | | | 251/181 |
| 3,058,718 A | 10/1962 | Johnson | |
| 3,213,888 A | 10/1965 | Cameron et al. | |
| 3,331,392 A | 7/1967 | Davidson et al. | |
| 3,490,736 A | 1/1970 | Snyder | |
| 3,913,886 A * | 10/1975 | Di Cicco | F16K 5/0407 |
| | | | 251/215 |
| 4,258,750 A | 3/1981 | Schnall et al. | |
| 4,705,669 A | 11/1987 | Tsuji et al. | |
| 5,344,392 A * | 9/1994 | Senninger | A61M 1/287 |
| | | | 604/4.01 |
| 5,590,686 A | 1/1997 | Prendergast | |
| 6,196,267 B1 | 3/2001 | Rutz | |
| 6,520,481 B2 * | 2/2003 | Harneit | F16K 5/103 |
| | | | 137/599.17 |
| 6,808,162 B2 | 10/2004 | Tranovich et al. | |
| 6,845,966 B1 * | 1/2005 | Albizuri | F16K 5/162 |
| | | | 251/207 |
| 6,863,257 B2 | 3/2005 | Home | |
| 6,975,924 B2 | 12/2005 | Kircher et al. | |
| 7,036,793 B2 * | 5/2006 | Turnau, III | F16K 5/0414 |
| | | | 251/175 |
| 7,620,479 B2 | 11/2009 | Kircher et al. | |
| 8,146,884 B2 * | 4/2012 | Yli-Koski | F16K 5/0407 |
| | | | 251/209 |
| 8,146,888 B1 * | 4/2012 | Hoeptner | F16K 5/0414 |
| | | | 251/310 |
| 9,328,922 B2 * | 5/2016 | Deng | F23Q 9/00 |
| 9,816,627 B2 * | 11/2017 | Gur | F16K 5/103 |
| 2001/0020488 A1 | 9/2001 | Ishii et al. | |
| 2004/0194834 A1* | 10/2004 | Rehder | F16L 41/03 |
| | | | 137/625.27 |
| 2004/0221904 A1 | 11/2004 | Usher et al. | |
| 2006/0048830 A1 | 3/2006 | Tokuda et al. | |
| 2006/0208213 A1* | 9/2006 | Turnau, III | F16K 5/0414 |
| | | | 251/309 |
| 2013/0322201 A1 | 12/2013 | Hitchcock et al. | |
| 2014/0024995 A1 | 1/2014 | Seaver et al. | |

* cited by examiner

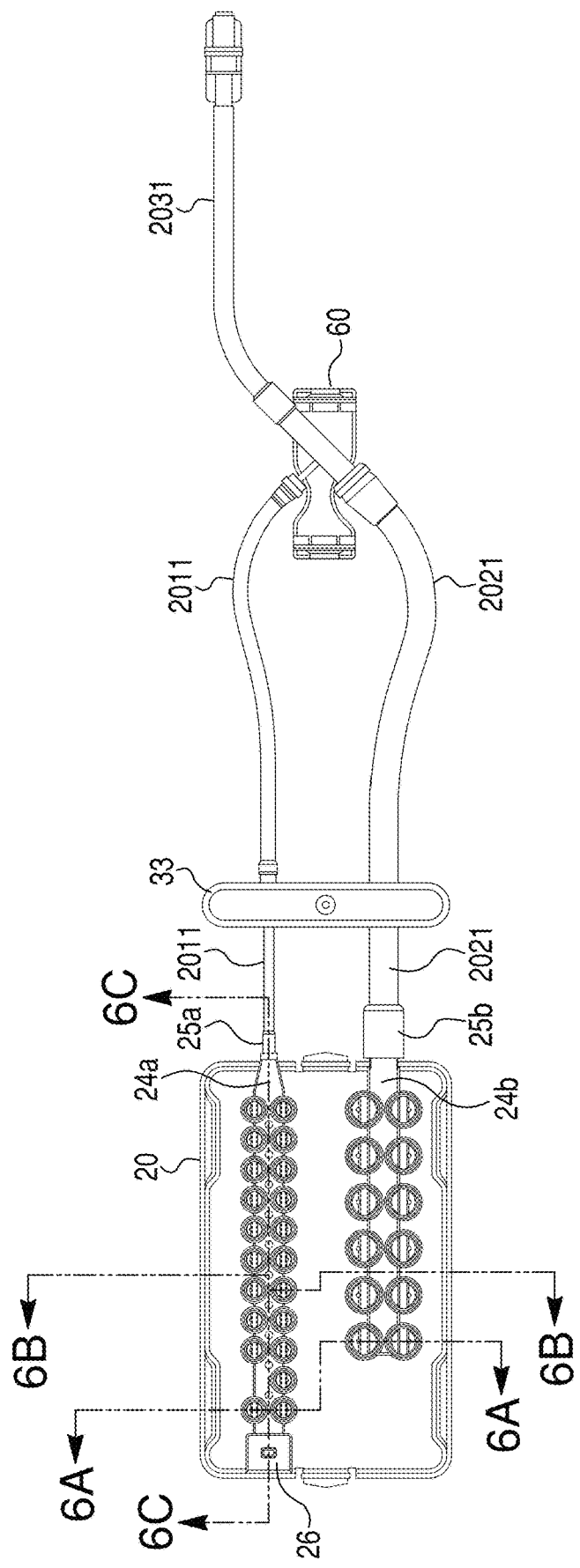

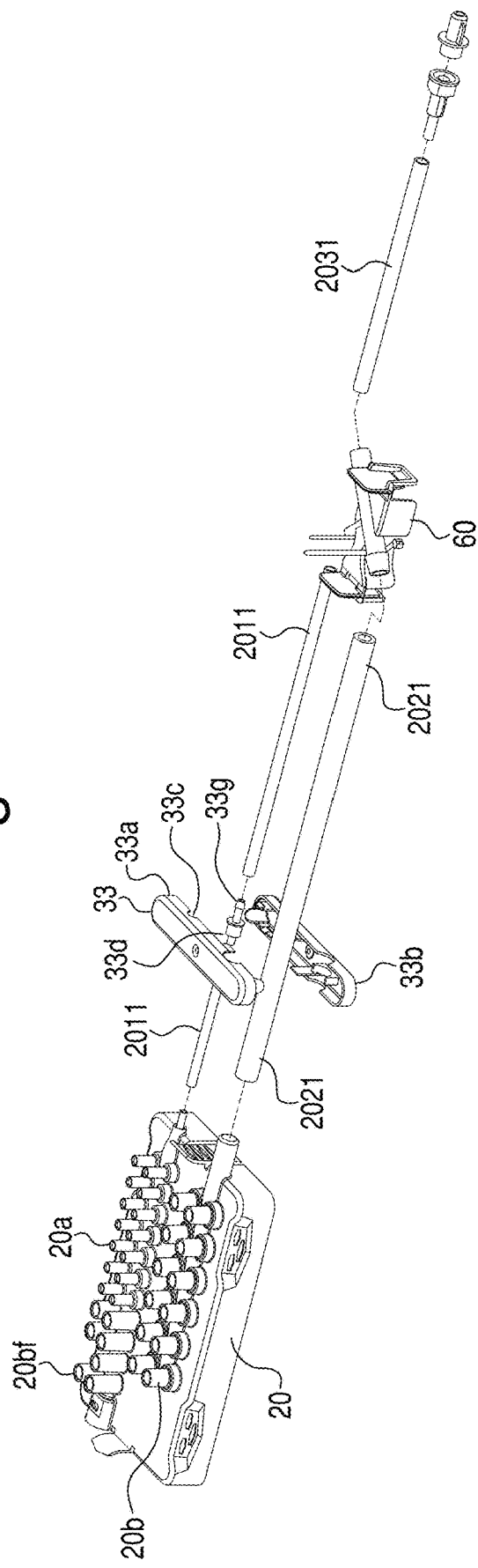

2. Confirm that transfer set manifold is not installed.

3. Secure manifold and confirm manifold is attached to device.

4. Secure strain relief in sensor block.

5. Confirm sensor block door is closed.

6. Route tubing around pump rotors and secure union junction to device.

7. Confirm that platens are closed and locked.

8. Close pump door.

 Pump Calibration
1. Confirm the calibration final container is attached and marked Not For Patient Use 
2. Calibrate macro pump 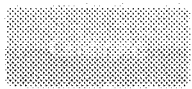
3. Confirm macro pump calibration 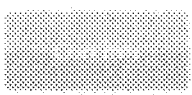
4. Calibrate micro pump 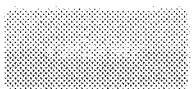
5. Confirm micro pump calibration 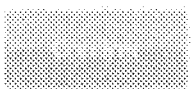
 
Fig. 26

Fig. 28

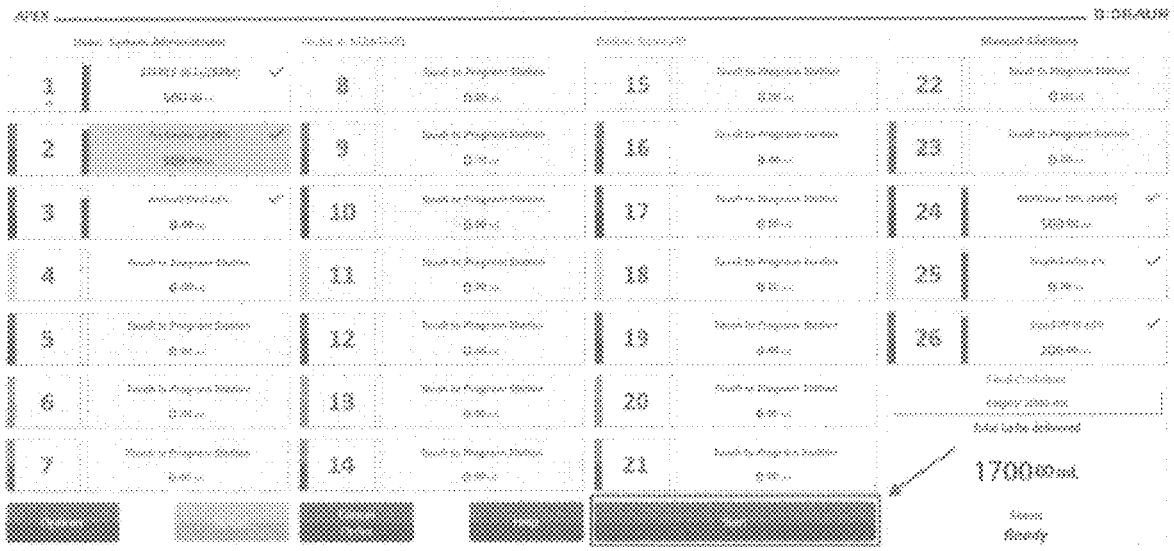
Fig. 30
 Low Volume Warning
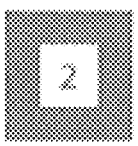 FreAmine III 10% : 56.00mL Required
Insufficient volume remaining for automated dispense.
Manually dispense remaining volume or replace source.
Fig. 31

Fig. 34

COMPOUNDING DEVICE, SYSTEM, KIT, SOFTWARE, AND METHOD

This application is a continuation of and claims the priority benefit under 35 U.S.C. § 120 of U.S. patent application Ser. No. 15/490,372 filed on Apr. 18, 2017 which in turn claims priority to U.S. patent application Ser. No. 14/797,000 filed on Jul. 10, 2015 now U.S. Pat. No. 9,623,389 issued on Apr. 18, 2017, and U.S. patent application Ser. No. 15/478,313 filed on Apr. 4, 2017 now U.S. patent Ser. No. 10/512,885 issued on Dec. 24, 2019, and to U.S. patent application Ser. No. 14/693,867 filed on Apr. 23, 2015, U.S. patent application Ser. No. 14/700,779 filed Apr. 30, 2015 now U.S. Pat. No. 9,802,171 issued on Oct. 31, 2017, U.S. patent application Ser. No. 14/719,936 filed May 22, 2015 now U.S. Pat. No. 10,143,985 issued on Dec. 4, 2018, and U.S. patent application Ser. No. 14/731,042 filed Jun. 4, 2015 now U.S. Pat. No. 9,802,172 issued on Oct. 31, 2017, which are all hereby incorporated in their entireties by reference.

BACKGROUND

1. Field

The presently disclosed subject matter relates generally to devices, systems, software, kits, and methods for preparing admixtures of various fluids, such as pharmaceuticals, assays, nutritional fluids, chemicals, and other fluids, for administration to human, animal, plant, mechanical/electrical/chemical/nuclear systems, or other users. In one exemplary embodiment, the disclosed subject matter can relate to devices, systems, software, kits and methods in which a plurality of parenteral ingredients are mixed or compounded together for delivery to a patient or user via an infusion or intravenous bag (e.g., for intravenous, intra-arterial, subcutaneous, epidural, or other transmission).

2. Description of the Related Art

Compounding involves the preparation of customized fluid ingredients including medications, nutritional liquids, and/or pharmaceuticals, on a patient-by-patient basis. Compounded medications and solutions can be made on an as needed basis whereby individual components are mixed together to form a unique solution having the strength and dosage needed by the patient. This method allows the compounding pharmacist to work with the patient and/or the prescriber to customize a medication to meet the patient's specific needs. Alternatively, compounding can involve the use of a compounding device to produce compounds in an anticipatory fashion, such as when a future or imminent demand for a particular combination of medicaments or pharmaceuticals or other compound components is known. Further, compounding devices can be used to produce pooled bags, for example, that include certain fluids that are needed for either a number of patients or for the same patient for a number of days or a number of administrations. Thus, the pooled bag(s) can be used by including further specific compounding components, if any, either for a specific patient or for a specific timing for the same patient.

Compounding devices typically use three types of measuring methods: gravimetric (e.g., additive gravimetric (weight final container) or subtractive gravimetric (weight the source containers as the pump delivers)), volumetric, or a combination of gravimetric and volumetric where each type can be used to check the other type. Compounders can be further broken down into three categories based on the minimum volumes they can deliver and the number of components they can accommodate: macro, micro, or macro/micro. Compounders typically have a stated minimum measurable volume and accuracy range. When compounding, higher volumes usually have larger absolute deviations, but lower percentage deviations. Operating software has been used to maximize the effectiveness and efficiency of compounding devices.

Gravimetric devices generally use a peristaltic pump mechanism combined with a weight scale or load cell to measure volume delivered. The volume delivered is calculated by dividing the weight delivered by the specific gravity of the ingredient. Gravimetric devices are not typically affected by running the source containers empty and delivering air into the final bag. These devices can be calibrated by using a reference weight for each ingredient. For example, the device's load cell can be calibrated using a reference mass on the load cell, and individual amounts of fluid dispensed measured by the load cell can be corrected based on the specific gravity of the fluid being dispensed.

Volumetric devices generally use both a peristaltic pump mechanism and a "stepper" motor to turn the pump mechanism in precisely measurable increments. The device calculates the volume delivered by the precision of the delivery mechanism, internal diameter of the pump tubing, viscosity of the solution, and the diameter and length of the distal and proximal tubing. Delivery from these devices can be affected by many factors including: variances in the pump tubing's material, length, elasticity, and diameter; temperature, which affects solution viscosity and tubing size; total volume pumped; ingredient head height; final bag height; position (e.g., initial and final positions) of the pump rollers relative to the pump platens; and empty source components. Thickness of the pump tubing can significantly affect delivery accuracy, and wear on the pumps over time can also cause diminishing accuracy.

Monitoring and replacing source containers before they are empty can prevent the volumetric devices from delivering air in lieu of the ingredient to the final container.

In some cases, due to injury, disease, or trauma, a patient may need to receive all or some of his or her nutritional requirements intravenously. In this situation, the patient will typically receive a basic solution containing a mixture of amino acids, dextrose, and fat emulsions, which can provide a major portion of the patient's nutritional needs. These mixtures are commonly referred to as parenteral mixtures ("PN"). Parenteral mixtures that do not include lipids are commonly referred to as total parenteral nutritional mixtures ("TPN"), while parenteral mixtures containing lipids are referred to as total nutritional admixtures ("TNA"). Often, to maintain a patient for an extended period of time on a PN, smaller volumes of additional additives, such as vitamins, minerals, electrolytes, etc., are also prescribed for inclusion in the mix.

Compounding devices facilitate the preparation of PN mixtures in accordance with the instructions provided by a medical professional, such as a doctor, nurse, pharmacist, veterinarian, nutritionist, engineer, or other. Compounding devices typically provide an interface that allows the medical professional to input, view, and verify the dosage and composition of the PN to be prepared and afterward confirm what had been compounded. The compounding device also typically includes source containers (i.e., bottles, bags, syringes, vials, etc.) that contain various solutions that can be part of the prescribed PN. The source containers can be hung from a framework that is part of the compounding device or can be mounted to a hood bar that is either part of or separate from the compounding device. A single pump or a plurality of pumps may be provided which, under the control of a controller, pump the selected solutions into a final container, for example, a receiving bag. The receiving bag is typically set on a load cell while being filled so that it can be weighed to ensure that the correct amount of solution is prepared. Once the bag has been filled, it can be released from the compounding device and, in this exemplary embodiment, can be used as a reservoir for intravenous infusion to a patient. Compounding devices are typically designed for operation in aseptic conditions when compounding pharmaceutical or neutraceutical ingredients.

When pharmaceuticals are used, a pharmacist can review instructions that are sent to the compounding device to ensure an improper mixture does not occur. The pharmacist can also ensure the specific sequencing of fluids/liquids is appropriate.

In the medical field, compounding devices can be used to compound fluids and/or drugs in support of chemotherapy, cardioplegia, therapies involving the administration of antibiotics and/or blood products therapies, and in biotechnology processing, including diagnostic solution preparation and solution preparation for cellular and molecular process development. Furthermore, compounding devices can be used to compound fluids outside the medical field.

Recently, there have been efforts to provide a compounding device that can operate more efficiently, with less downtime during source container replacement, and with increased usability features promoting more intuitive use of the system, as well as bubble and/or occlusion sensor mechanisms that cause fewer nuisance alarms.

SUMMARY

Accordingly, it may be beneficial to provide a compounding device, system, method, kit or software that operates more efficiently, improves set up time, and reduces downtime when an ingredient runs out and needs replacement, and which provides an aesthetically pleasing and intuitively operational structure, method of set up and use, and an associated usable, efficient and aesthetically pleasing computer interface. Certain embodiments of the disclosed subject matter also increase accuracy at small dispensed volumes, provide a form factor that promotes easier cleaning/disinfecting to maintain aseptic conditions, and also prevent errors, especially in transfer set/fluid path connections.

According to one aspect of the disclosure, a valve for use in a compounding device can include a valve housing and a valve structure located within the valve housing. The valve can be configured to permit fluid to flow through the valve when in an open position. The valve structure can include a gravity wall wherein, when the valve structure is in the open position, fluid moving through the valve structure moves upward against a force of gravity when travelling through the valve and traversing the gravity wall.

According to another aspect of the disclosure, a valve for use in a compounding device, can include a valve structure having a rotational axis and an input aperture located at a top of the valve structure and configured such that fluid entering the valve structure flows along a downward fluid path and substantially parallel with the rotational axis of the valve structure. The valve can include an exit aperture defined in a peripheral side wall of the valve structure and configured such that fluid exiting the valve structure flows along an exit path that is substantially perpendicular to the rotational axis of the valve structure. A gravity wall can be located within the valve structure and configured such that fluid travelling through the valve travels along the downward fluid path at an upstream side of the gravity wall, and travels on an upward fluid path on a downstream side of the gravity wall. The upstream side and downstream side of the gravity wall can be directly opposed to each other, and a direction of the downward fluid path can be generally opposed to a direction of the upward fluid path. When the valve structure is in an open position, fluid moving through the valve structure moves upward against a force of gravity when travelling through the valve and traversing the gravity wall.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 4A is a top view of an exemplary manifold, strain relief, union junction, and output line made in accordance with principles of the disclosed subject matter.

FIG. 4B is a perspective exploded view of the structures shown in FIG. 4A.

FIGS. 16-34 are screen shots of an exemplary controller interface for use with a compounding device or system made in accordance with principles of the disclosed subject matter.

DETAILED DESCRIPTION OF EXEMPLARY EMBODIMENTS

Figure 1:
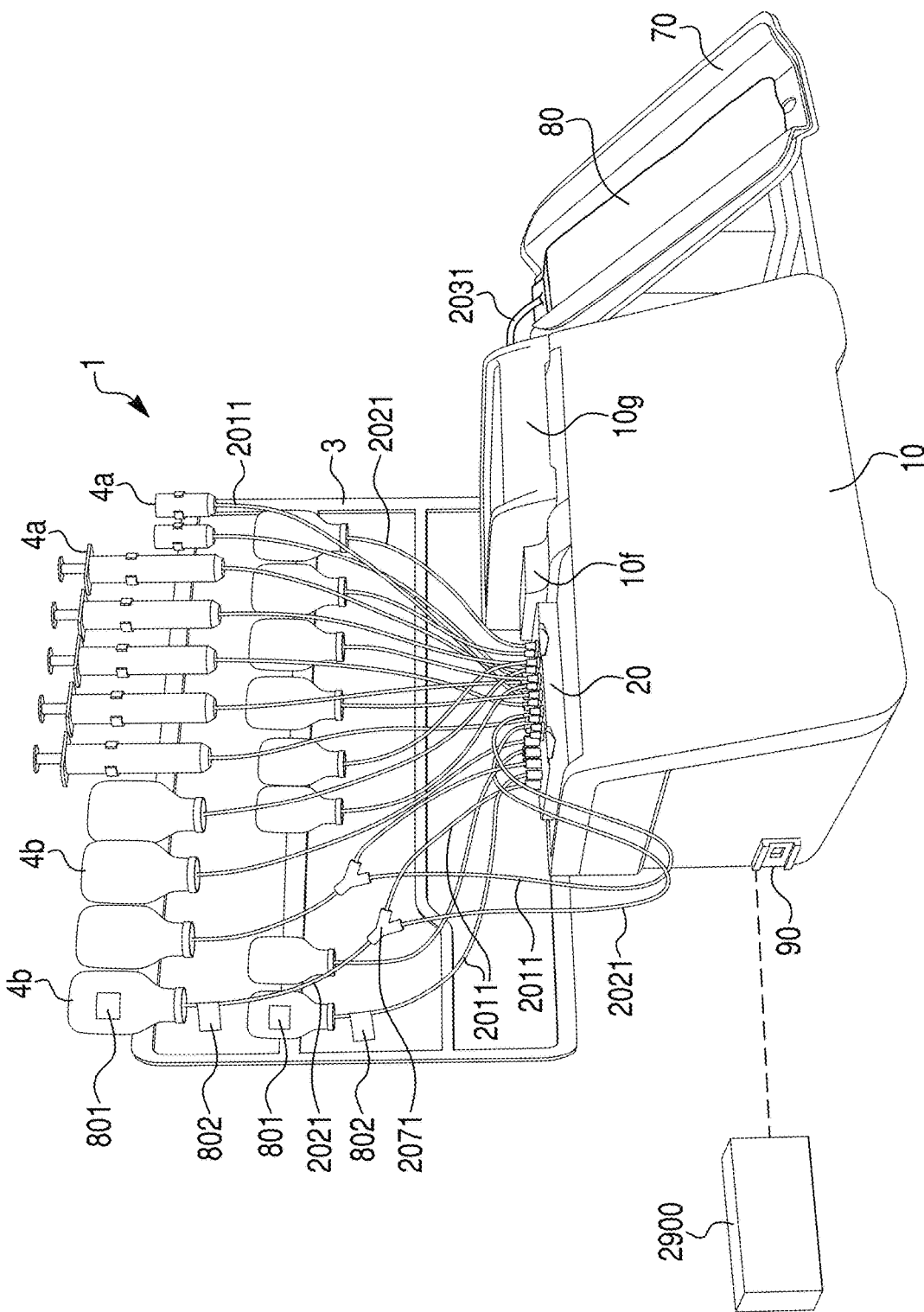
FIG. 1 is a perspective view of an exemplary embodiment of a compounding system made in accordance with principles of the disclosed subject matter.
Figure 2A:
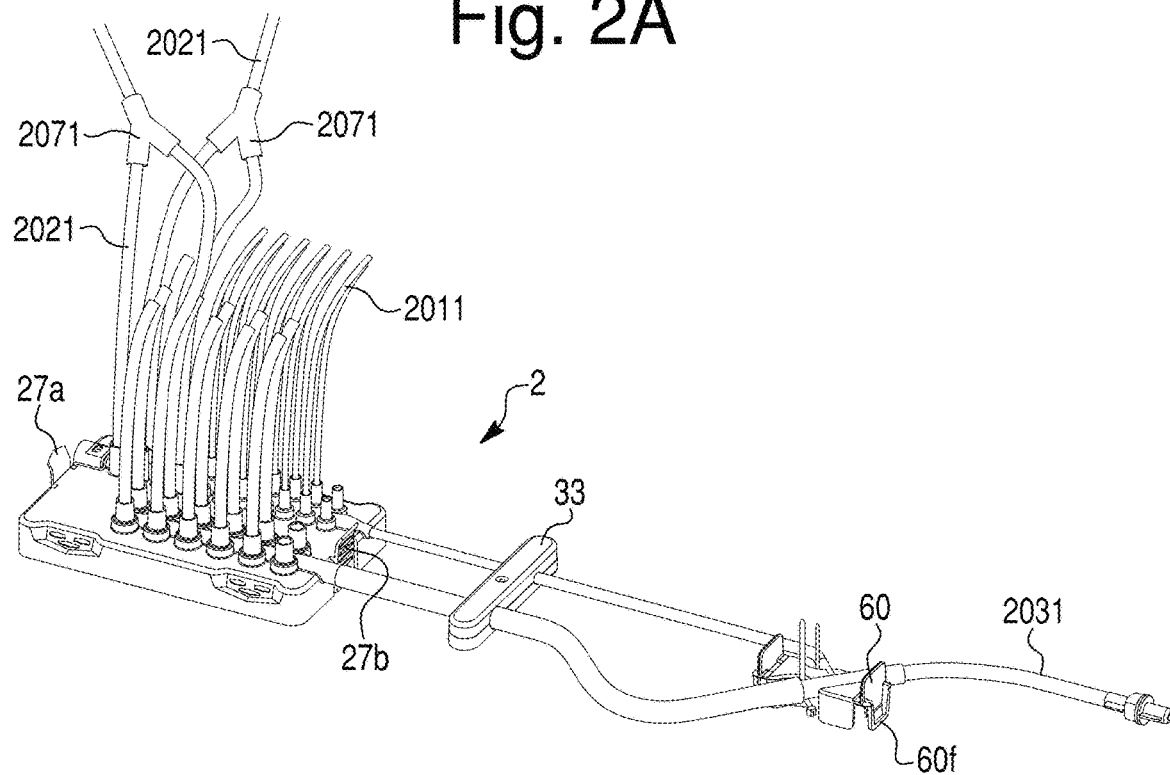
FIG. 2A is a perspective view of the exemplary transfer set of FIG. 1.
Figure 2B:
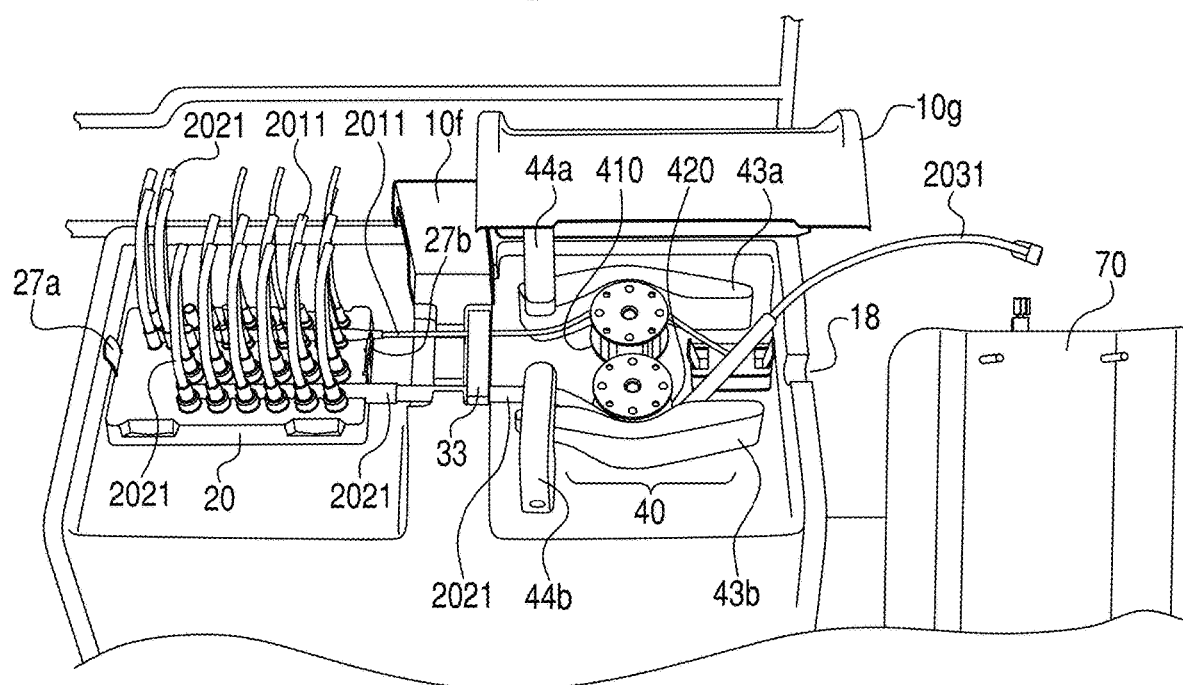
FIG. 2B is a partial perspective view of the exemplary embodiment of FIG. 1.

FIGS. 1 and 2B are two different perspective views of an exemplary embodiment of a compounding system 1 made in accordance with principles of the disclosed subject matter, with safety lids which are also hereinafter referred to as a sensor bridge cover 10f and a pump cover 10g in a closed position and opened position, respectively. The system 1 can be used to compound or combine various fluids from small or large containers 4a, 4b and consolidate the fluids into a single/final container, such as an intravenous fluid bag 80, for delivery to a human or animal patient, or to a lab for diagnostics, or to a storage facility for later sales or use. In one example, the system 1 can include a plurality of small supply containers 4a and large supply containers 4b each attached to an ingredient frame 3, a housing 10 having at least one pump (41, 42) (See FIG. 3A), a transfer set 2 (See FIG. 2A) that is selectively connectable to the housing 10 and that includes a manifold 20 attached to a plurality of micro input lines 2011, macro lines 2021, a controller connection 90, a controller 2900, and a discharge tray 70 in which a final container, such as IV fluid bag 80, can rest while connected to an output line(s) of the transfer set 2. The transfer set 2 is intended to be a sterile, disposable item. In particular, the transfer set 2 can be configured to create or compound many different mixtures or prescriptions into appropriate receiving bags 80 for a predetermined time or predetermined volume limit. Once the transfer set 2 reaches its predetermined time and/or volume limit, the set 2 can be disposed of and replaced by a new transfer set 2. In other words, the transfer set 2 is a pharmacy tool that is to be used for a full compounding campaign, for example, for a 24 hour compounding run in which prescriptions for multiple patients are filled during that time period. Before beginning a given compounding procedure, the operator loads the various components of the transfer set 2 to the housing 10 of the compounding device 1.

As shown in FIG. 1, the transfer set 2 (See FIG. 2A) can be connected (or connectable) between the at least one input container (such as micro container(s) 4a and/or macro container(s) 4b) and the output container (such as an IV fluid bag 80) via a plurality of lines (for example, micro input line(s) 2011 and/or macro line(s) 2021). The transfer set 2 can include a plurality of micro and macro lines 2011, 2021 extending therethrough, a manifold 20, a strain relief clip 33, a union junction 60 and an output line 2031. The micro and macro lines 2011, 2021 run through at least one manifold 20 such that fluids from each of the separate supply containers 4a, 4b can be at least partially mixed in the manifold 20 prior to further mixing at junction 60 located downstream of pump 40. The transfer set 2 is connectable to the main housing 10 of the system 1 and provides the connection between the input supply container(s) 4a, 4b and the output container. The housing 10 provides (among other features) pumping and control functionality to safely and efficiently select and deliver exact quantities of various fluids from containers 4a, 4b through the transfer set 2 to the output container. The manifold 20 can include two separate flow paths such that compounding can continue along a first flow path while the second flow path is interrupted.

The transfer set 2 macro lines 2021 and micro lines 2011 are all attached to specific inlet tubing ports (i.e., 20a and 20b) of the manifold 20. The free or upstream ends of these lines are each uniquely marked with a permanent identification tag 802. In this exemplary embodiment, the identification tag 802 is a bar coded flag or sticker. The identification tag 802 provides one-to-one traceability and corresponds to a specific instance of the inlet tubing port (20a or 20b) to which it is attached. The source containers 4a and 4b possess unique data identifying the type and kind of fluids contained therein. This data can also be formatted in bar code format and placed onto tag 801. During use, the attached source containers (i.e., 4a and 4b) can be linked in the controlling software to the specific lines 2011 or 2021 by linking the source container data on the bar code format located on tag 801 to the bar code (or other identification information) located on the attached line identification tag 802. Once connected, correlated and linked in this way, when the compounding device requires the specific ingredient, the software links established above determines which valve actuator 102a' or 102b' must be turned in order to introduce the required or intended source fluid into the compounded receiving bag 80.

Connection of the transfer set 2 to the main housing 10 can be initiated by connecting the manifold 20 to the housing 10. The manifold 20 can include a plurality of ports, such as micro input line port(s) 20a and/or macro input line port(s) 20b. The lines of the transfer set 2 can include a plurality of lines, such as micro lines 2011 and/or macro lines 2021 and/or combination micro/macro line(s) referred to as flex line(s). The plurality of lines can correspondingly connect to the above-referenced micro container(s) 4a and/or macro container(s) 4b at an input end of respective micro and macro line(s) 2011, 2021. An output end of each of the micro and macro line(s) 2011, 2021 can be connected to the manifold 20. The manifold 20 can be selectively connected to the housing 10 such that at least one valve 21a, 21b located in the manifold 20 can be aligned with a valve actuator 102a' and 102b' that can be incorporated in a stepper motor 102a, 102b located in the housing 10 (which will be described in more detail below).

Figure 3A:
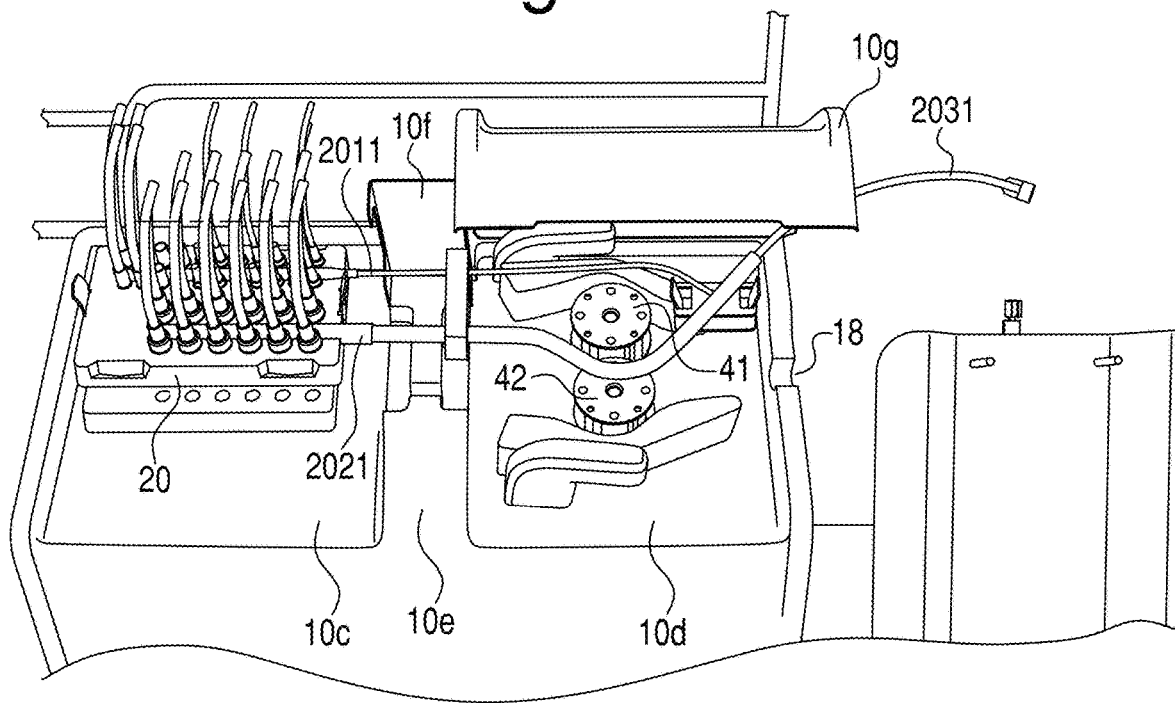
FIGS. 3A-G are partial perspective views of the exemplary embodiment of FIG. 1 in sequential positions in which an exemplary transfer set including manifold and output lines are aligned and connected to exemplary valve actuators, sensor block and pumps.
Figure 3B:
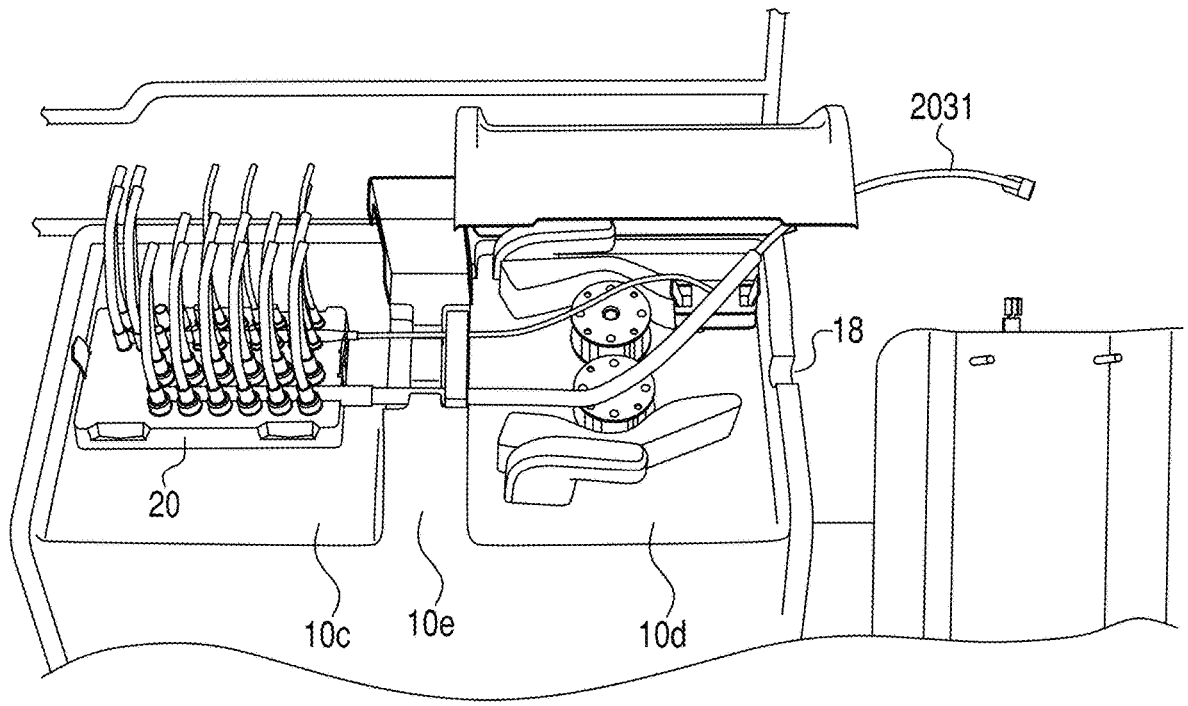

In this exemplary embodiment, as shown in FIGS. 3A and 3B, when installing the transfer set 2 onto housing 10, the manifold 20 is connected to a top left side of housing 10 within a shallow tray indent 10c in the upper surface of the housing 10. The shallow tray 10c allows spilled fluids or leaks to run off the pump housing 10 in order to prevent ingress of the fluids to the internal electronics and mechanisms of the compounding system 1. In FIG. 3A, transfer set 2 and manifold 20 are not yet in position and are located above the housing 10 as if a user is starting the process of placing the transfer set 2 onto the housing 10 and preparing for use of the compounding system 1. The transfer set 2 includes a manifold 20 that has two distinct channels: a first channel 24a that connects to a plurality of micro lines 2011 and/or macro lines 2021, and a second channel 24b that connects to a plurality of macro lines 2021. Of course, in other embodiments the first and second channels could each be connected solely to micro, macro, flex, or other types of lines, respectively, or could be connected to combinations of micro, macro, or other types of lines. The first channel 24a and the second channel 24b are located in the manifold 20 and can be completely separate from each other (i.e., in fluid isolation from each other), such that no fluid from the first channel 24a mixes with fluid from the second channel 24b. The channel is considered that portion or area in the manifold through which fluid can flow. In this embodiment, a micro outlet 25a and a macro outlet 25b can be located on a downstream side of manifold 20 and connected to micro line 2011 and macro line 2021, respectively. It should be noted that the lines downstream of the manifold (e.g., outlet lines, or micro line 2011 and macro line 2021) can incorporate different tubing as compared to the inlet lines 2011, 2021 that supply fluid to the manifold 20. For example, the inlet lines can include tubing made of more or less rigid material as compared to the outlet lines, and can also include tubing made with larger or smaller diameter openings, or made of larger or smaller side wall thicknesses. In addition, the color of the inlet lines can be different from the color of the outlet lines, and the lines can also have different surface textures either inside or outside of the tubing. For example, the texture on the inside could be configured to promote or prevent turbulence, depending on the application and location of the line.

A sensor structure 29 can be located in the manifold (See FIGS. 7A and 7B) and is configured to trip a sensor 2901 (See FIG. 15) located in the housing 10 that tells the system that the manifold 20 is in a correct/operational position. Alternatively, the sensor 2901 can be configured to confirm the presence and gross positional information for the manifold 20, but not necessarily configured to confirm that the position is fully operational. The sensor structure 29 can include a magnet 29m that goes into a housing 29h and provides a signal to (or actuates) the sensor 2901 in the housing 10 which indicates that manifold 20 and transfer set 2 are properly (i.e., securely) in place (See FIG. 7A). Software used with the system can be configured such that the compounder 1 will not operate/function when sensor 2901 does not sense or is not actuated by the magnet 29m (i.e., when the manifold 20 is not in proper position with respect to the housing 10). After the manifold 20 is secured to the housing by clips 27a, 27b located on opposing ends of the manifold 20 (See FIG. 2B), a strain relief clip 33 can be seated onto the housing. The strain relief clip can be pre-assembled and attached to both the micro line 2011 and macro line 2021. When installed, the strain relief can be placed to the right and immediately adjacent a sensor bridge 10e that forms a right wall of the shallow manifold tray indent 10c in which the manifold 20 is seated. The strain relief clip 33 can be pre-assembled to the transfer set 2 to ensure ease of use by the end user.

Figure 3C:
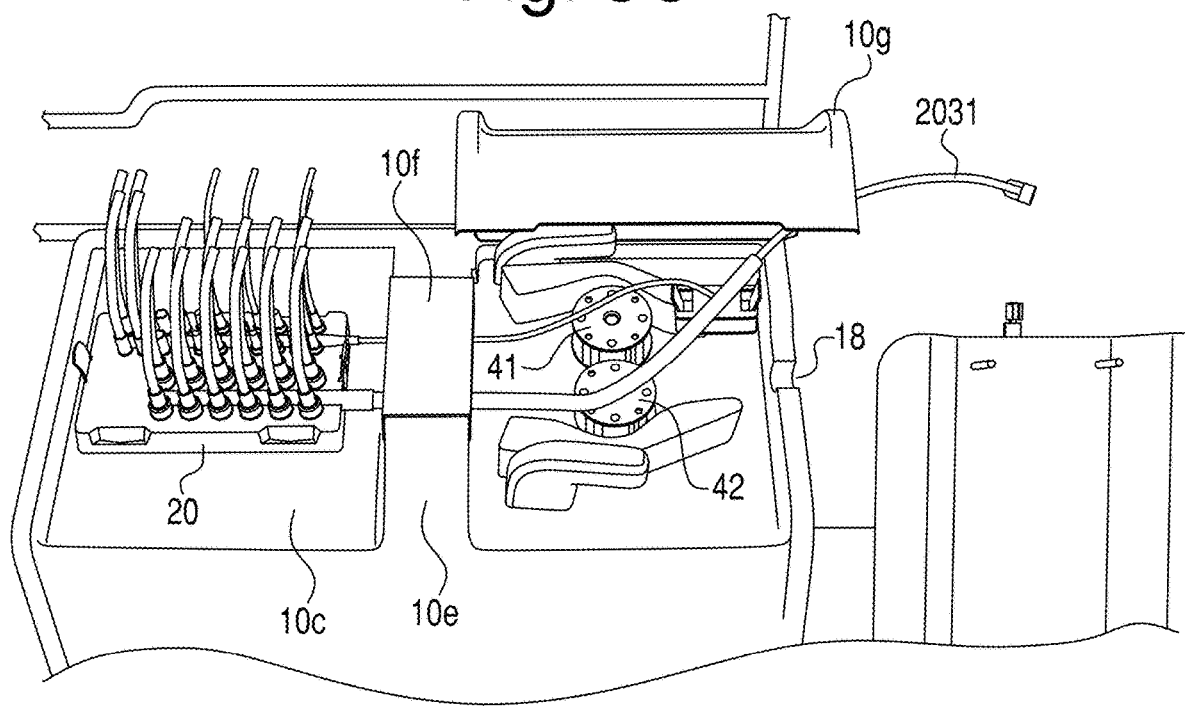

As shown in FIG. 3C, once the manifold 20 is attached to the housing 10 and the strain relief clip 33 is in place, the sensor bridge cover 10f can be closed over the sensor bridge 10e in order to protect the sensors and strain relief clip 33 from inadvertent contact and/or contamination from dust, liquids or other contaminants. The sensor bridge 10e can include a sensor or sensors (for example, an ultrasonic sensor, photo sensor, or other sensor) acting as a bubble detector and/or occlusion detector.

Figure 3D:
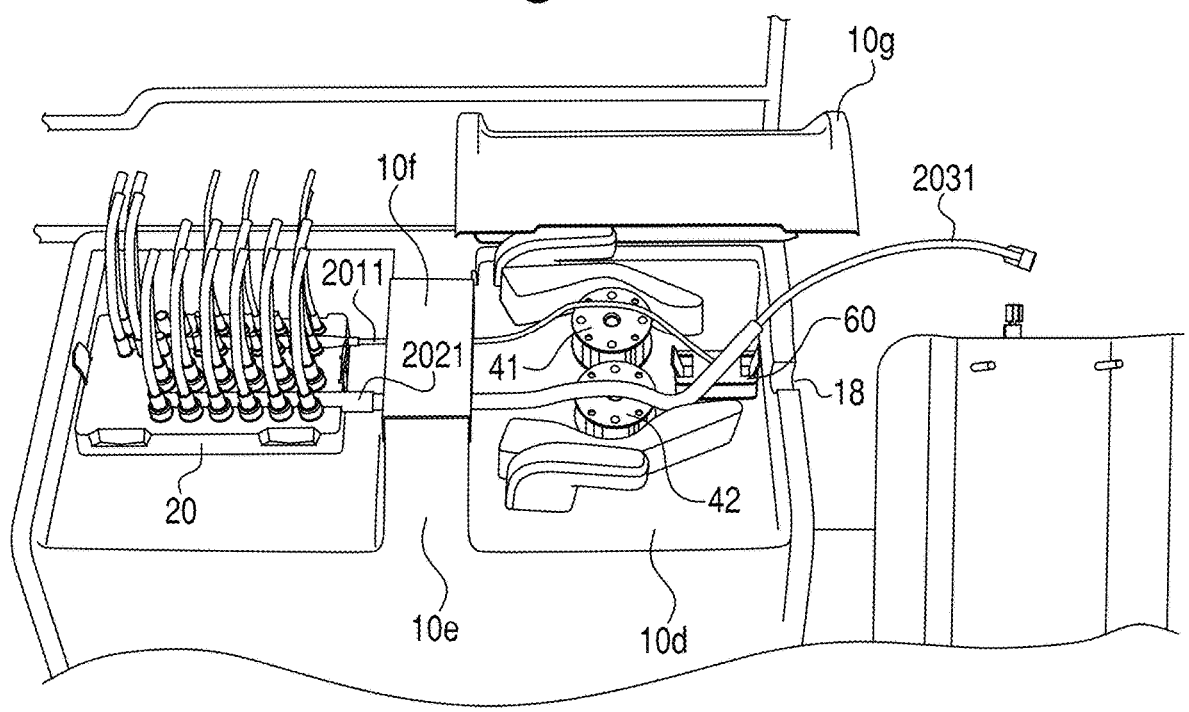

FIG. 3D shows an exemplary next step of installing the transfer set 2, which includes connecting the union junction 60 to the housing by snapping clip locks 60f (see FIGS. 10 and 11) located on the junction 60 to mating locks formed on an upper surface of the housing 10 and to the right of the pump 40. The output line 2031 can be set within an output guide 18 (See FIG. 3A) formed in an outer wall that defines a second shallow pump tray indent 10d in the upper surface of the housing in which the pump 40 is located.

Figure 3E:
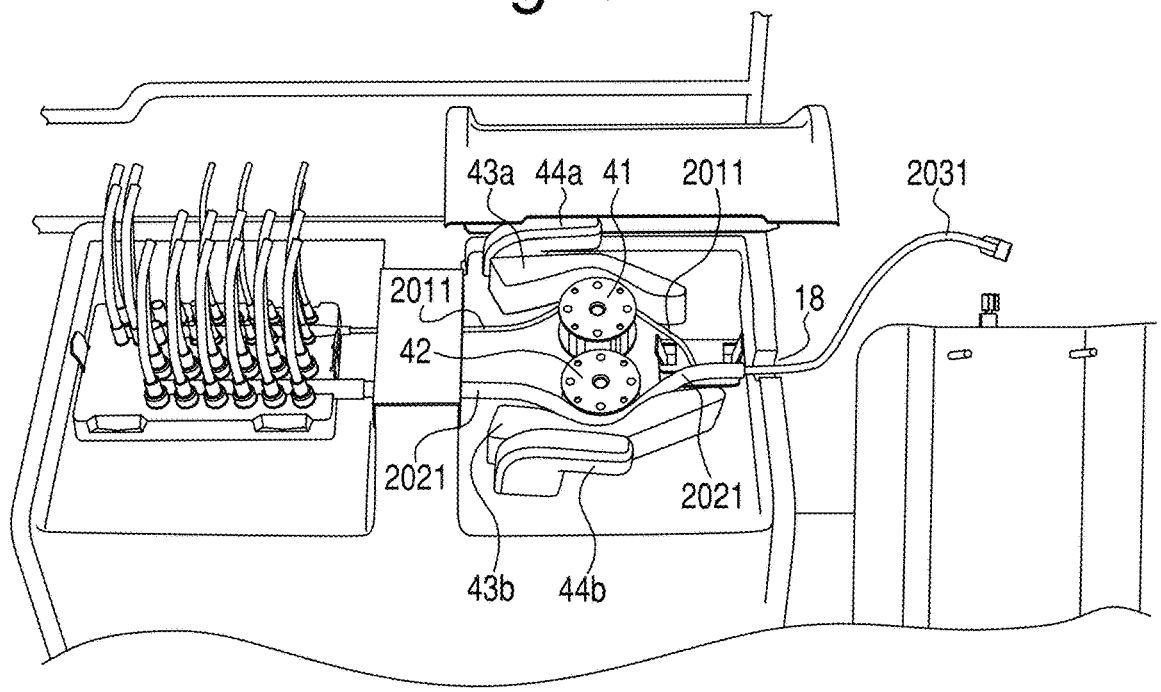

As shown in FIG. 3E, once the junction 60 and output line 2031 are in place, the micro line 2011 and macro line 2021 can be seated within the peristaltic pump 40. Alternatively, the union junction 60 can also be snapped into place after installing the pump tubing around each rotor 41, 42. In particular, micro line 2011 can be placed about the outer periphery of first rotor 41 and macro line 2021 can be placed about the outer periphery of second rotor 42. In this position, the micro line 2011 will be located between the first/micro rotor 41 and the first/micro platen 43a, and the macro line 2021 will be located between the second/macro rotor 42 and the second/macro platen 43b.

Figure 3F:
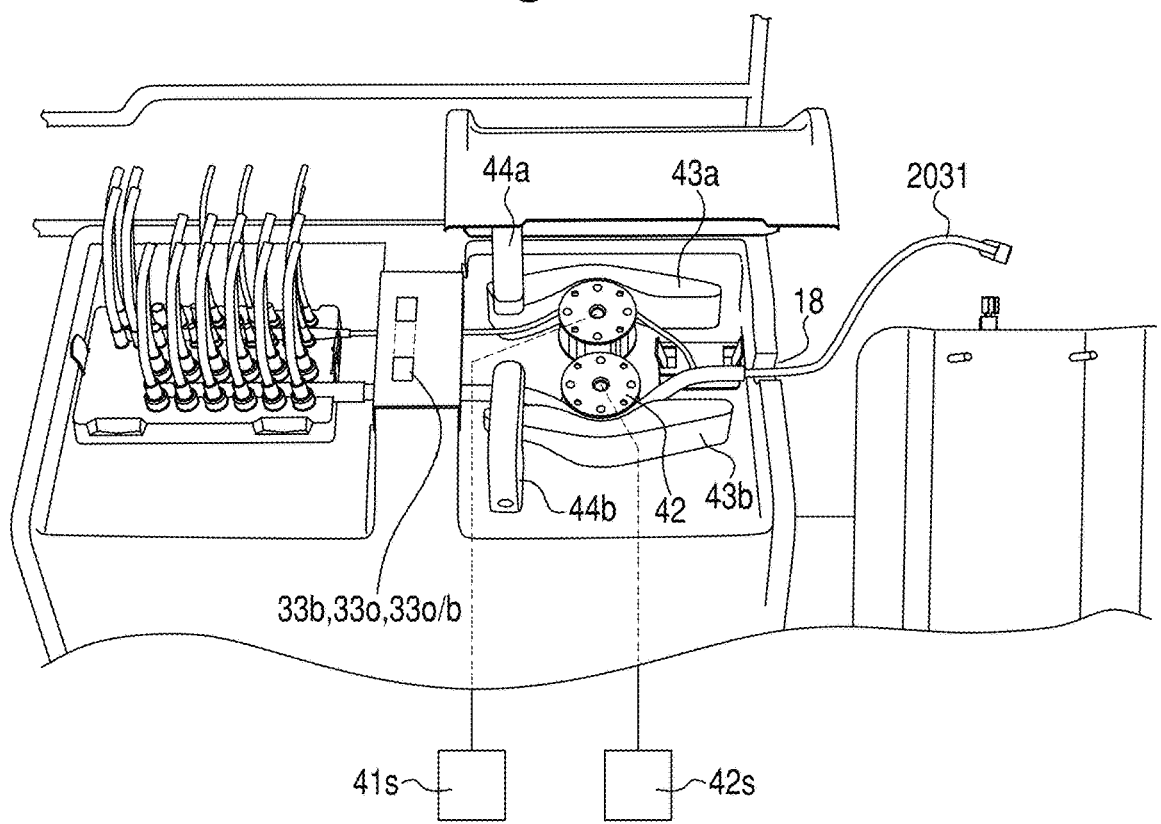

FIG. 3F shows an exemplary next step for connecting the transfer set 2 to the housing 10, which includes rotating the first/micro platen lock 44a clockwise to lock the platen 43a at its closed position relative to the first rotor 41, and rotating the second/macro platen lock 44b counter-clockwise to lock the second platen 43b at its closed position relative to the second rotor 42. In this position, when the rotors 41 and 42 are actuated and when any one of the valves 21a, 21b are rotated to the open position, each of the rotors will draw fluid(s) through respective lines 2011, 2021 through peristaltic forces/actions. If one of the valves 21a or 21b is not opened and the pump rotor operates, the peristaltic forces will create a vacuum between the manifold channels 24a, 24b inside the micro lines 2011 or macro lines 2021 between the manifold 20 and the pump rotors 41, 42 possibly resulting in an occlusion of the affected line. The occlusion will be detected as the wall of the micro lines 2011 and macro lines 2021 will partially collapse and this will be measured by the occlusion sensor within the sensor bridge 10e. The occlusion sensor 33o can be an optical sensor, a force based sensor, pressure sensor, an ultrasonic sensor or other known sensor for determining whether an occlusion has occurred in the line. In another embodiment, an occlusion sensor 33o and a bubble sensor 33b can be incorporated into the sensor bridge 10e. Alternatively, a combined sensor 33o/b or sensors 33o, 33b can be incorporated into the strain relief 33, or at other locations along the system 1, and can be integrated into the strain relief 33 or bridge 10e or can be separate and independent structures that are attached to the system 1.

Figure 3G:
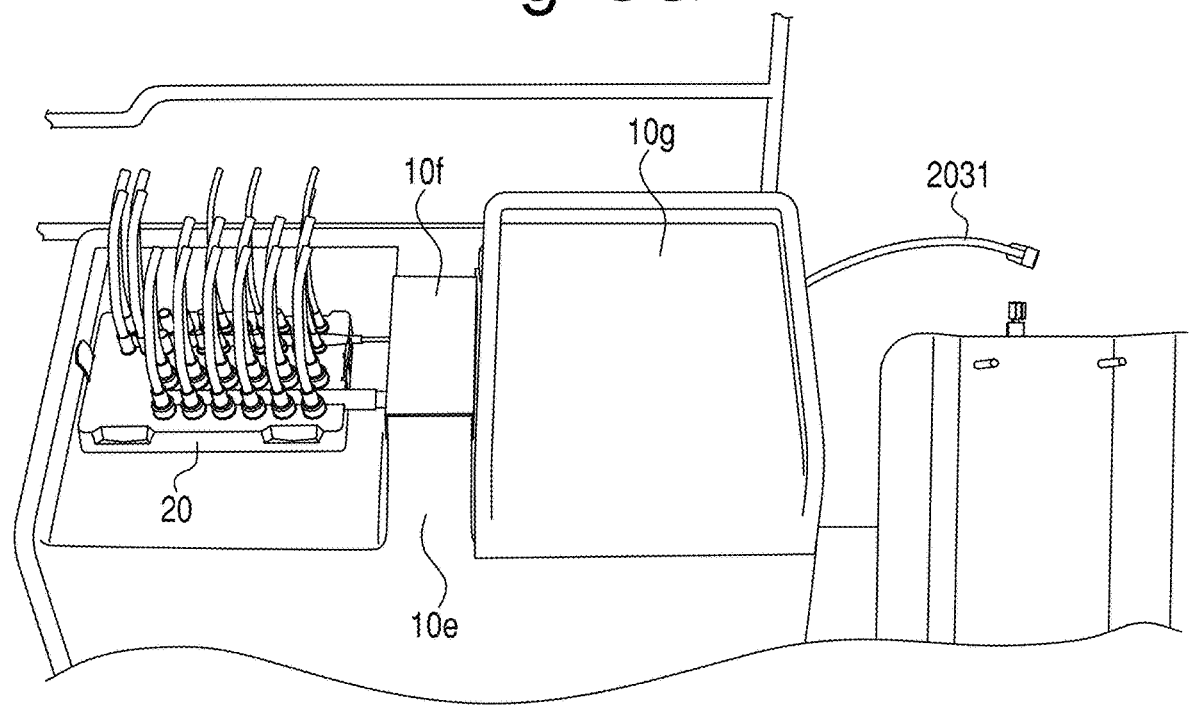

FIG. 3G shows an exemplary final step in the setup of the system 1, in which the pump cover 10g is closed over the pump 40 to protect the pump 40 from contact with other devices/structures/persons and to protect the pump 40 and associated lines 2011, 2021 from contamination from dust, liquids, or other contaminants. Each of the sensor cover 10f and pump cover 10g can include a magnet or other type of sensor or locking mechanism to ensure the covers are in place during operation of the system 1.

Once the transfer set 2 is correctly connected to the housing 10, input/storage containers 4a, 4b, and receiving bag 80, and the covers 10f and 10g are closed, calibration of the system 1 and then processing and compounding of various fluids can take place.

Figure 3H:
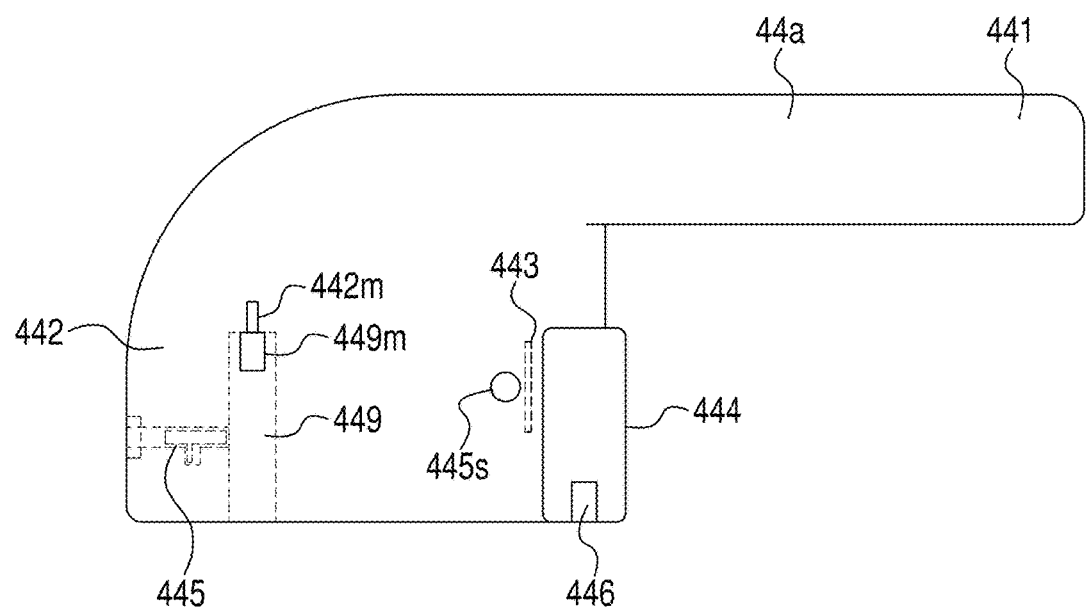
FIG. 3H is a side view of the platen lock shown in FIGS. 3A-3F.

FIG. 3H depicts an exemplary embodiment of a platen lock 44a. The platen lock 44a can be configured to rotate about a rotational axis and cause a cam 444 to come into resilient contact with the platen 43a. The cam 444 can include a biasing member, such as, for example, a spring 443, including, but not limited to, a plate spring, coil spring, or other type of spring to cause the cam 444 to keep in constant contact with and apply a preset and constant force to the platen 43a, which in turn keeps a constant or preset force on the micro line 2011 located between the platen and the rotor 41 to ensure accurate and predictable volumetric output by the pump 40 over the life of the transfer set. The spring 443 can be an important factor in the wear of the tubing lines during compounding, which can also impact the output of the pump 40.

Accuracy can also be a function of pump tubing inner diameter, tubing wall thickness, and the spacing between rollers and platen. Accuracy is also affected by the speed of rotation, but both motors can have the same accuracy.

The platen lock 44a can have a streamlined appearance, being configured substantially as a simple, L-shaped structure with an overhang upper extension 441 and a rotational lower extension 442. The lower extension having a longitudinal axis about which the platen lock 44a rotates. The platen lock 44a can be made from aluminum or other rigid material such as plastics, ceramics and/or other metals or alloys. The simple structure provides a user a sense of efficiency in the nature of operation of the platen lock structure 44a. The lower extension 442 can be configured with an opening to slide onto and attach to rotational post 449 extending from/within the housing 10. The platen lock 44a can lock onto the post 449 via a simple friction fit, a spline type relationship between the post 449 and the opening in the lower extension 442, or other structural configuration. In an alternate embodiment, a set screw structure 445 can be provided in the lower extension 442 for quick connection to the rotational post 449 that extends from the housing 10 of the compounding system 1. In the embodiment depicted in FIG. 3H, a set screw 445s can be used to set the preload on the spring 443 that is contained inside the platen lock 44a, 44b. This spring 443 applies force on the platen 43a, 43b and ultimately squeezes the platen 43a, 43b against the respective rotor 41, 42. A magnetic lock structure 449m and 442m can also (or alternative to the screw structure 445) be provided and can have multiple functions, including: locking the platen lock 44a to the housing 10 to prevent removal of the platen lock 44a from the housing 10 until the magnetic locks 449m and 442m are released. The location of platen lock 44a with respect to platen 43a can be achieved by a detent position on the backside of the platen 43a. As the platen lock 44a is rotated against the platen 43a towards the lock position, the cam 444 follows a profile on the back of the platen which includes a raised feature to compress the cam 444, which the user has to rotate past to reach the final lock position. The action of the cam over this feature provides feedback to the user that the lock point has been reached, and mechanically maintains this lock position due to the cam sitting in a cavity feature. Continued rotation past the desired lock point can be prevented by providing hard stop geometry in the platen profile such that the cam cannot get past the hard stop geometry. The location of the cam 444 when the platen lock 44a is in this lock position, is where sensor 2904a is tripped via a magnet 446 embedded in the bottom of cam 444. The coupling of lock arm 44a to the post 449 is achieved via a pair of magnets, the first 449m embedded in the top of post 449, the second 442m at the end of the receiving bore in the lower extension 442 of the lock arm 44a.

Another benefit of this exemplary embodiment of the system 1 is that the configuration allows the operator to easily remove the platens 43a, 43b and platen lock components 44a, 44b from the pump housing for cleaning without the use of tools. Both platens 43a, 43b can be removed by simply pulling them upward and away from the pump housing surface 10d.

In addition, both rotors 41, 42 can be removed without tools by simply unscrewing thumb screws that can be provided at a center/rotational axis of the rotors 41, 42. Because the rotors 41, 42 can be interchangeable, their life can be extended by swapping their positions after cleaning, e.g., macro to micro and micro to macro.

The pump 40 can include rotors 41, 42 that are each mounted upon and separately rotated by a respective stepper motor 41s, 42s (See FIG. 3F). Each of the stepper motors 41s, 42s can have a preset microsteps per revolution value that is relatively high (for example, on the order of $10^3$ greater than the microsteps per revolution value for the stepper motors 102a, 102b used to rotate valves 21a, 21b located in manifold 20, as described in more detail below). The high value of microsteps per revolution for the stepper motors 41s, 42s allows for greater accuracy or precision in fluid delivery for the system 1. Each of the stepper motors 41s, 42s can be connected to controller 2900 and can be separately, sequentially, serially, concurrently or otherwise controlled to cause each of the rotors 41, 42 to rotate a known and predetermined amount and possibly at a predetermined speed such that a highly accurate amount and timing of material flow through the compounding device can be achieved. In addition, steppers 41s, 42s can be provided with absolute encoders that are in communication with controller 2900 to provide explicit positioning control of the steppers 41s, 42s.

The rotors 41, 42 can be substantially identical to each other such that they can be interchanged. For example, in one embodiment, the macro rotor 42 can be configured to rotate more than the micro rotor 41 and will thus be subject to higher wear. Thus, at some point during a break in operation of the compounding system 1, the macro rotor 42 can be interchanged with the micro rotor 41 such that the rotor 41 will act as the macro rotor and be subject to the heightened wear for a time period. In this manner, the life of both rotors 41, 42 can be extended.

The cam 444 and the spring 443 can also be configured to provide a known force to the platen 43a when the platen lock 44a is in a certain rotational position such that the platen lock 44a is effectively locked in place due to both resilient forces and frictional forces that occur when at the certain position relative to the platen 43a. In other words, once the platen lock 44a passes a predetermined rotational position, resilient force acting on the platen lock 44a by the platen 43a tends to cause the platen lock to continue its clockwise rotation. A sensor, such as a magnet 446, can be provided in the platen lock 44a and configured to trip a corresponding sensor 2904a in the housing 10 that tells the system the platen lock 44a is in the correct position. However, if there is a rotational stop located in either the post in the housing or the lower extension 442, the platen lock 44a will be unable to rotate further in the clockwise rotational direction and will simply maintain the above-referenced known resilient force (due to cam 444 and cam spring 443) with the resilient force also acting to prevent release of (counterclockwise rotation of) the platen lock 44a. Unlocking the platen lock 44a from the platen 43a in this case would simply require the operator to overcome the resilient and frictional forces of the cam in the detent position tending to hold the structures in place. It should also be noted that the platen lock 44b and platen 43b can be configured in a similar manner as described above with respect to the platen lock 44a and platen 43a, except that locking would occur in a counterclockwise rotational motion.

FIGS. 4A and 4B show a portion of an exemplary transfer set 2 that includes a manifold 20 connected via micro line 2011 and macro line 2021 to a strain relief clip 33. Micro line 2011 and macro line 2021 extend past the strain relief clip 33 and eventually combine or merge at the union junction 60, resulting in a single outlet line 2031 for the transfer set 2. The macro lines 2021 can be portions of the same continuous tubing structure. By contrast, in this example, micro lines 2011 are separate structures joined together by shunt 33g. The shunt 33g can be made from a material that is harder than the micro lines 2011. For example, the micro lines 2011 can be made from silicone tubing while the shunt 33*g* can be made from a relatively more rigid PVC material. The shunt 33*g* provides extra rigidity such that the strain relief clip 33 can connect securely thereto without causing the inner diameter of the shunt 33*g* to be squeezed or otherwise reduced. One or more collars 33*d* can be provided on the shunt 33*g* to lock to the clip 33 and prevent the shunt 33*g* from moving along a longitudinal axis of the micro lines 2011. Additional collars are contemplated so that manufacturing can be easier with respect to consistently locating/assembling of the manifold set structures. By contrast, the macro line 2021 can be sufficiently large enough in diameter and thickness such that its inner diameter is not squeezed or reduced when the clip 33 is attached thereto. Thus, when the strain relief clip 33 is attached to the micro lines 2011 and macro line 2021, the clip 33 does not significantly change the inner diameter characteristics for the lines while preventing forces acting along the longitudinal axes of the lines from being transmitted past the clip 33. Thus, when the micro line 2011 and macro line 2021 are connected about a respective rotor 41, 42 of the peristaltic pump 40, the rotary forces acting on the lines do not translate along the micro and macro input lines back towards the manifold 20 and the bubble and occlusion sensors. The strain relief clip 33 acts as a damper to minimize transmission of linear forces and vibrations from the pump 40 to the manifold 20. Minimizing these forces and vibrations optimizes the functionality of the bubble and occlusion sensors, which would otherwise be impacted by changes in tubing tension as the tubing is pulled by the peristaltic action of the pump. Similarly, the strain relief provides a fixed position on the set 2 relative to the manifold 20 to facilitate installation of the tubing or line segments through the occlusion and bubble sensors 33*o*, 33*b*, 33*o/b* and maintains a repeatable tension on these line segments.

Figure 5:
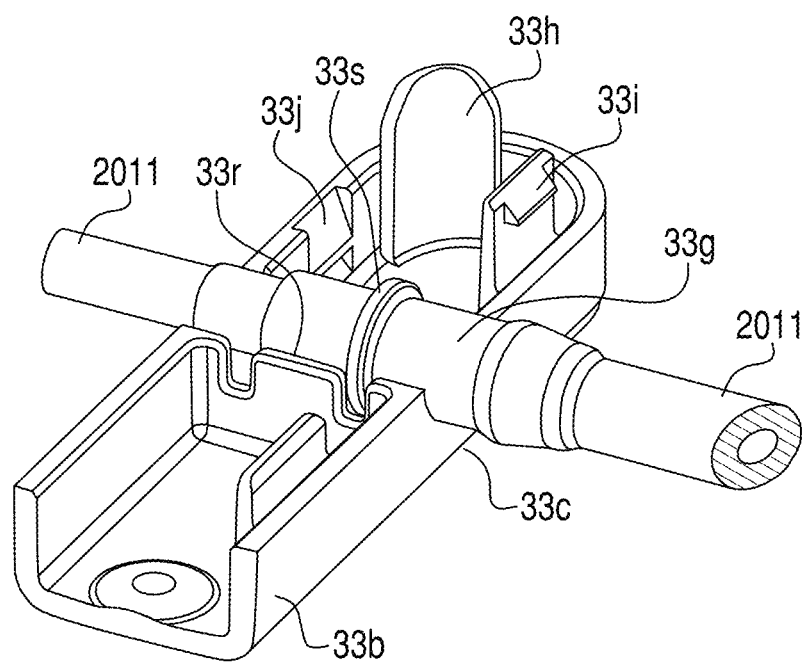
FIG. 5 is a partial perspective view of the strain relief shown in FIG. 4A.

The strain relief clip 33 can be of various shapes, and in the embodiment shown in FIG. 5 the clip 33 is configured as a two piece clam shell type design in which an upper portion 33*a* can be attached to a lower portion 33*b* by clips 33*i* that are integrally formed at locations about a perimeter of each portion 33*a* and 33*b*, and mate with snap latch receptacles 33*j* in an opposing portion 33*a*, 33*b*. Throughways 33*c* can be formed as half cylindrical cutouts in the upper portion 33*a* and lower portion 33*b*. A guide sleeve 33*h* can be provided at a corner of one of the clam shell portions 33*a*, 33*b* to guide the opposing claim shell portion 33*a*, 33*b* into engagement when coupling the clam shell portions 33*a*, 33*b*. The micro line 2011 and macro line 2021 can pass through these throughways 33*c* and be locked to the strain relief clip 33 by a series of ridges 33*r* that connect to mating ridge 33*s* in the shunt 33*g* and/or to the macro line 2021 itself. It is possible that the strain relief parts 33*a* and 33*b* are in fact identical so that the above described process and configuration is possible with the use of two instances of the same component.

Figure 6A:
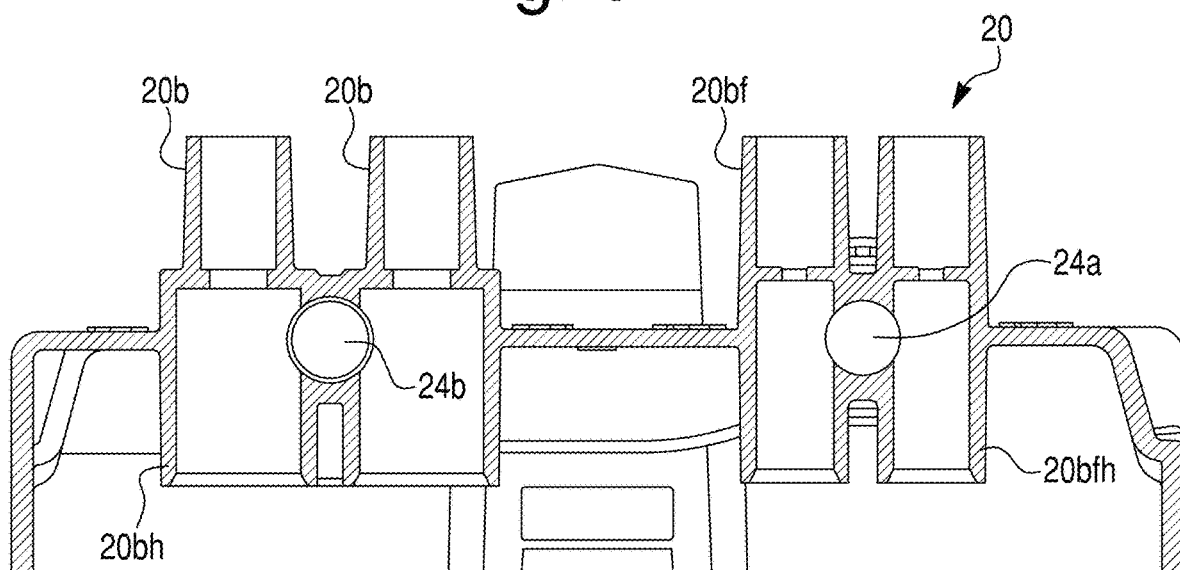
FIGS. 6A-C are cross section views taken along lines 6A, 6B, and 6C of FIG. 4A, respectively.
Figure 6B:
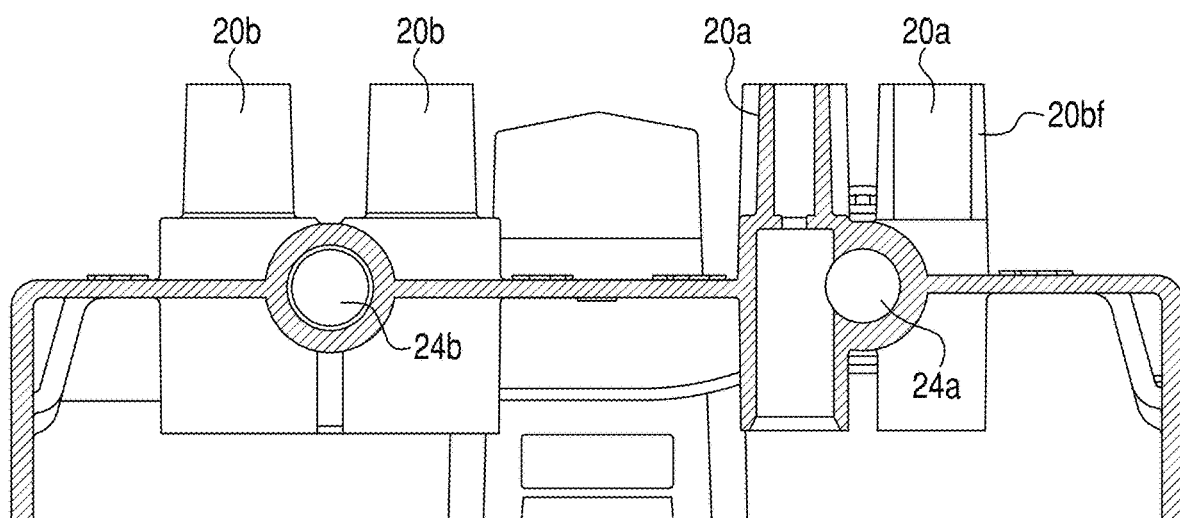
Figure 6C:
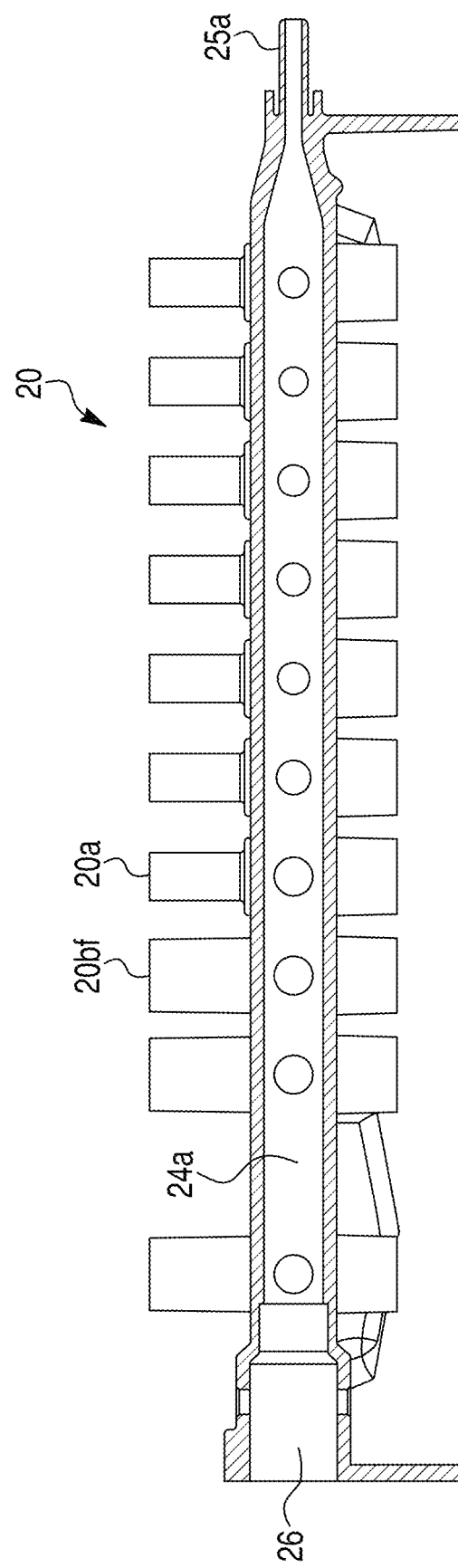

FIGS. 6A-6C show various cross-sections of the exemplary manifold 20 of FIG. 4A without valve structures located therein for clarity. The cross section shown in FIG. 6A depicts two sets of ports: two macro ports 20*b* and two flex ports 20*bf* that are each cylindrical in shape and are in fluid communication with a valve housing 20*bh* and 20*bfh*, respectively, located immediately underneath the ports 20*b* and 20*bf*. The ports 20*b* and 20*bf* are configured such that a macro line 2021 can be slid into the inner periphery of the upward and outward facing cylindrical opening in the ports 20*b* and 20*bf* for attachment thereto. Thus, the ports 20*b* and 20*bf* can be connected to various macro source containers 4*b* via the lines 2021 attached to the ports 20*b* and 20*bf*. A valve 21*b*, 21*a* (to be described in more detail below) can be located within the valve housing 20*bh*, 20*bfh*, respectively, located beneath the ports 20*b*, 20*bf*. When the valve 21*b*, 21*a* is located in the housing 20*bh*, 20*bfh*, the valve 21*b*, 21*a* selectively connects the fluid located in line 2021 with the fluid located in channel 24*b*, 24*a* of the manifold depending on the valve's rotational position within the housing 20*bh*, 20*bfh*.

The manifold described above can, in the exemplary embodiment, be formed (e.g., molded) as one unitary structure 20 including all of the features 20*a*, 20*b*, 20*bf*, 20*ah*, 20*bh*, 20*bfh*, 24*a*, 24*b*, 25*b*, 26, 27*a*, 27*b*, and 29. Also, it is possible to join any or all separate structures (components) 20*a*, 20*b*, 20*bf*, 20*ah*, 20*bh*, 20*bfh*, 24*a*, 24*b*, 25*b*, 26, 27*a*, 27*b*, and 29 in any combination into a manifold assembly 20 to achieve the same purpose.

Figure 7A:
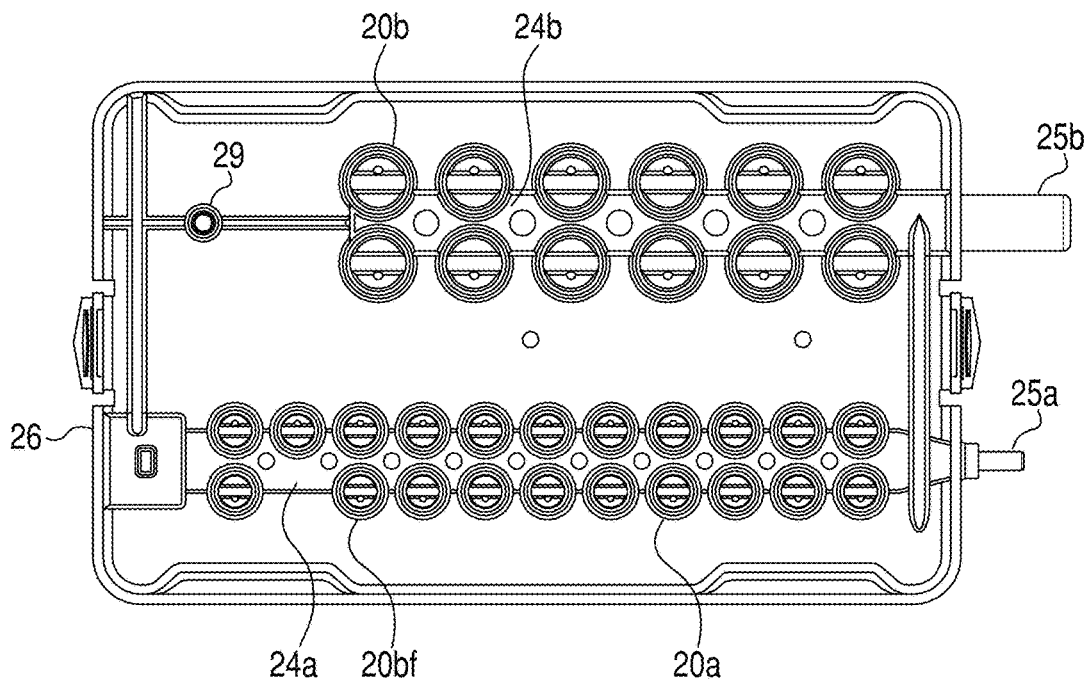
FIGS. 7A-C are a bottom, perspective exploded, and perspective assembled view, respectively, of the manifold of FIG. 1.
Figure 7B:
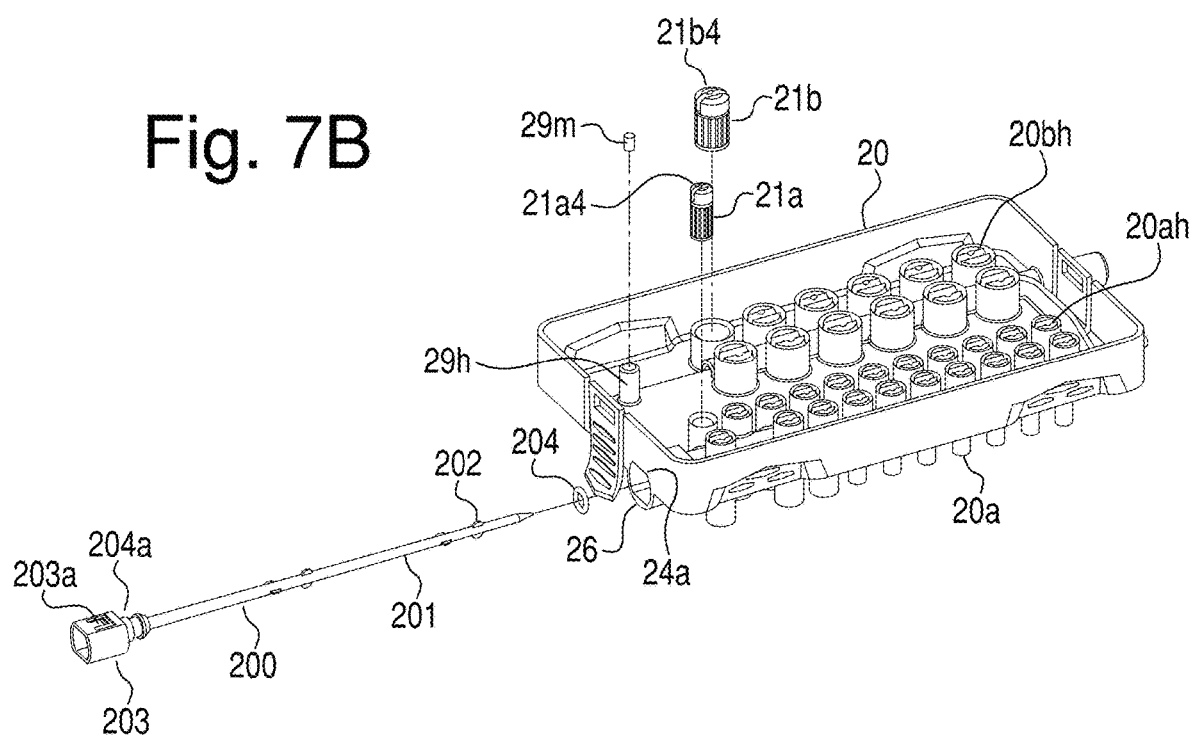
Figure 7C:
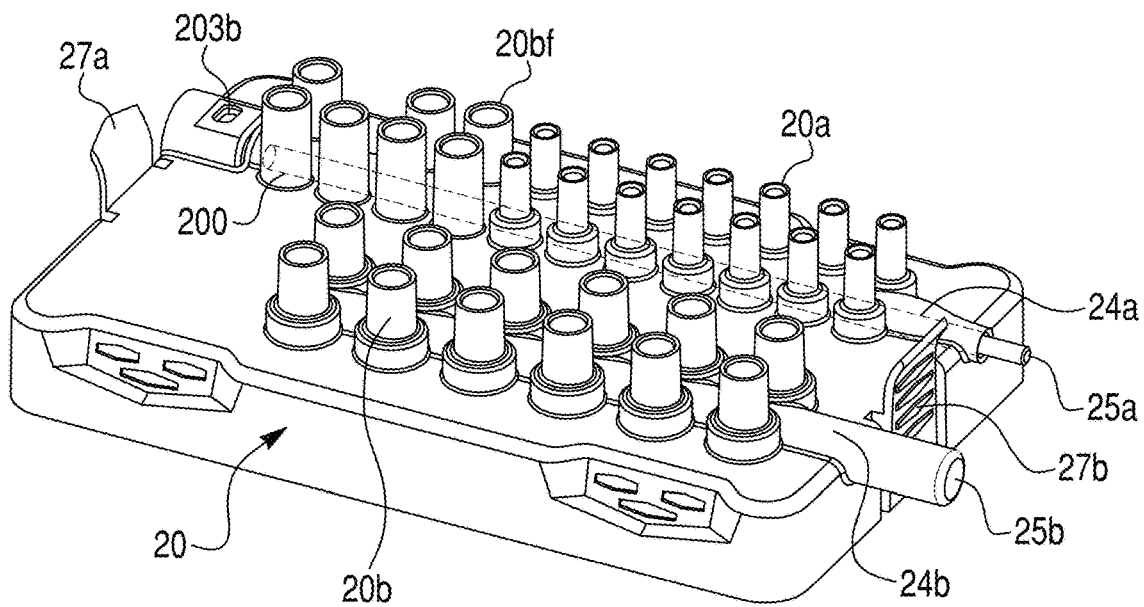

FIGS. 7A-C show a bottom view of the manifold 20, an exploded view, and an assembled view, respectively. The manifold 20 includes an array of macro ports 20*b* located in a linear fashion along either side of second channel 24*b*. The first channel 24*a* includes both flex ports 20*bf* and micro ports 20*a* located along the length thereof and provides fluid communication therebetween. Thus, the first channel 24*a* can be connected to both a macro flex line 2021 and a micro line 2011. In this embodiment, the flex line is configured as shown in FIG. 1 as a first macro line 2021 that is joined at a junction 2071 to two outgoing macro lines 2021 to allow fluid from macro container 4*b* to be supplied to both the first channel 24*a* and second channel 24*b*. In other words, a jumper branch connection in a macro line 2021 can be provided such that the macro line 2021 branches in two directions after leaving the macro storage container 4*b*, and can be connected to both the second channel 24*b* and the first channel 24*a*. The flex line conducts the same fluid/solution (e.g., nutritional ingredient) from container 4*b* to both channels 24*a* and 24*b* of the manifold 20 after passing through the valves 21*bf* and 21*b*, respectively. This facilitates the option of a singular or larger source container 4*b* being used for purposes of flushing/clearing the channels 24*a* and 24*b* as opposed to two separate containers 4*b*, wherein one container is connected to channel 24*a* and a separate other container is connected to channel 24*b*. A plurality of flex lines can be used since multiple types of flushing ingredients may be required during a compounding campaign depending on the varying clinical needs of the intended final contents of sequentially filled receiving containers (e.g. final bags 80). It should be noted that in this embodiment flex lines are terminated at flex ports 20*bf* (See FIG. 6B) farthest along the channels 24*a* and 24*b* from the outlets 25*a* and 25*b*, thereby allowing the entire channels 24*a* and 24*b* to be flushed with the flushing ingredient. In this embodiment, the micro line 2011 is not branched after leaving the micro storage container 4*a*, and therefore, there are no micro ports 20*a* that communicate with the second channel 24*b*. It is contemplated that an embodiment of the disclosed subject matter could include a manifold configured with valves adapted to allow micro lines to be attached to both the first and second channels 24*a* and 24*b*. Flex lines are designed to be used for any ingredient, which may be requested across a wide range of volumes among different patient prescriptions. Hence, for some prescriptions where they are requested in small volumes, they can be delivered by the micro pump. Similarly, for prescriptions where they are requested in large volumes, they can be delivered by the macro pump. The y-connection fluid path of the flex line gives the ingredient access to both fluid paths (micro and macro) therefore the system can decide which pump to use to deliver that ingredient appropriately based on the requested volume.

In FIG. 7B, the valves 21a, 21b and filler 200 are disassembled to better show their relationship with the macro valve housing 20bh, micro valve housing 20ah, and first channel 24a in which each of these structures resides when assembled and ready for use. As can be seen, each of the valves 21a and 21b include a keyway 21a4 and 21b4, respectively, that allows for positive attachment to an actuator member 102a' and 102b' that extends from a manifold indent/surface 10c in the housing 10 of the compounding device.

The operational valve structures are in fact combinations of the rotating members (valves 21a and 21b) and the inner diameter (ID) of the socket in the manifold (20ah and 20bh) in which the valves 21a, 21b are located. The configuration of the operational valve structures was intended to create a more moldable elastomeric valve in which, under static fluid conditions, gravity based movement of fluids (like the motion caused by fluids of differing densities or different specific gravities settling or rising when the valve is left open) can be prevented or limited.

The actuator member is controlled by at least one stepper motor 102a, 102b such that rotation of the valves 21a and 21b can be precise. In one embodiment, the stepper motor 102a for the micro valves 21a can be of higher precision than the stepper motor 102b for the macro valves 21b (See FIG. 9). Higher precision stepper motors can be used to provide the positional accuracy of the micro valves 21a due to the inherent flexibility of the micro valves 21a. For example, a stepper that has a preset value of about 48 microsteps per revolution can be used (which preset value can be on the order of $10^3$ less than the microsteps per revolution value for the pump). Accuracy of the valves 21a, 21b (i.e., precise movement of the valves 21a, 21b) can be further controlled through the use of a tall gear box, which would result in large input rotations for the stepper motors 102a, 102b providing for small movement of each of the valves 21a, 21b, respectively. The flexibility of material that makes up each of the valves 21a, 21b can be configured or selected to enhance or provide improved sealing surfaces which withstand pressure differentials without leaking. The valves 21a, 21b can be made from a first material having a first elasticity value, and the valve housing 20ah and 20bh can be made from a second material having a second elasticity value, and the first elasticity value being greater than the second elasticity value, wherein each valve 21a, 21b is more elastic than the valve housings 20ah, 20bh. Given this torsional flexibility and considering the friction opposing rotation of the micro valve 21a, it follows that during rotation, the upper features of the valve, i.e., those opposite the drive slots 21a4, angularly lag behind the lower features of the valve. Thus, in order to properly place the fluid opening between the valve 21a and the channel 24a, the higher precision stepper motors first rotate the valve 21a so that the top of the valve is properly positioned, and then reverse direction to bring the lower features also into proper position and therefore straightening the valve. The same action returns the valve to the closed position. The rotation of the steppers 102a and therefore the actuators 102a' and the valve 21a, can be clockwise, counter-clockwise, or any combination of these directions. Because, the micro valves 21a typically control the smaller volume ingredients, the volume should be measured and distributed with relatively higher accuracy as compared to that of the macro valves 21b which typically distribute large volume ingredients in which high accuracy is easier to achieve. However, it should be understood that accuracy of delivery is not necessarily a direct function of valve operation. As long as the valves are properly opened and closed, the pumps 41, 42 can be used to provide accuracy of amount and control of fluid delivery.

In operation, the micro valves 21a and macro valves 21b can be described as being overdriven by the stepper motors past the 'open' position since the valves are flexible and the top of the valve lags behind the bottom of the valve when rotated. Thus, to properly open the valve, the bottom of the valve is overdriven from the target angular position. Once the top has achieved a proper location, the stepper reverses and brings the bottom of the valve into proper position. This operation effectively twists and then straightens the valve, and occurs in both the opening and closing process for the valves 21a, 21b.

Figure 9:
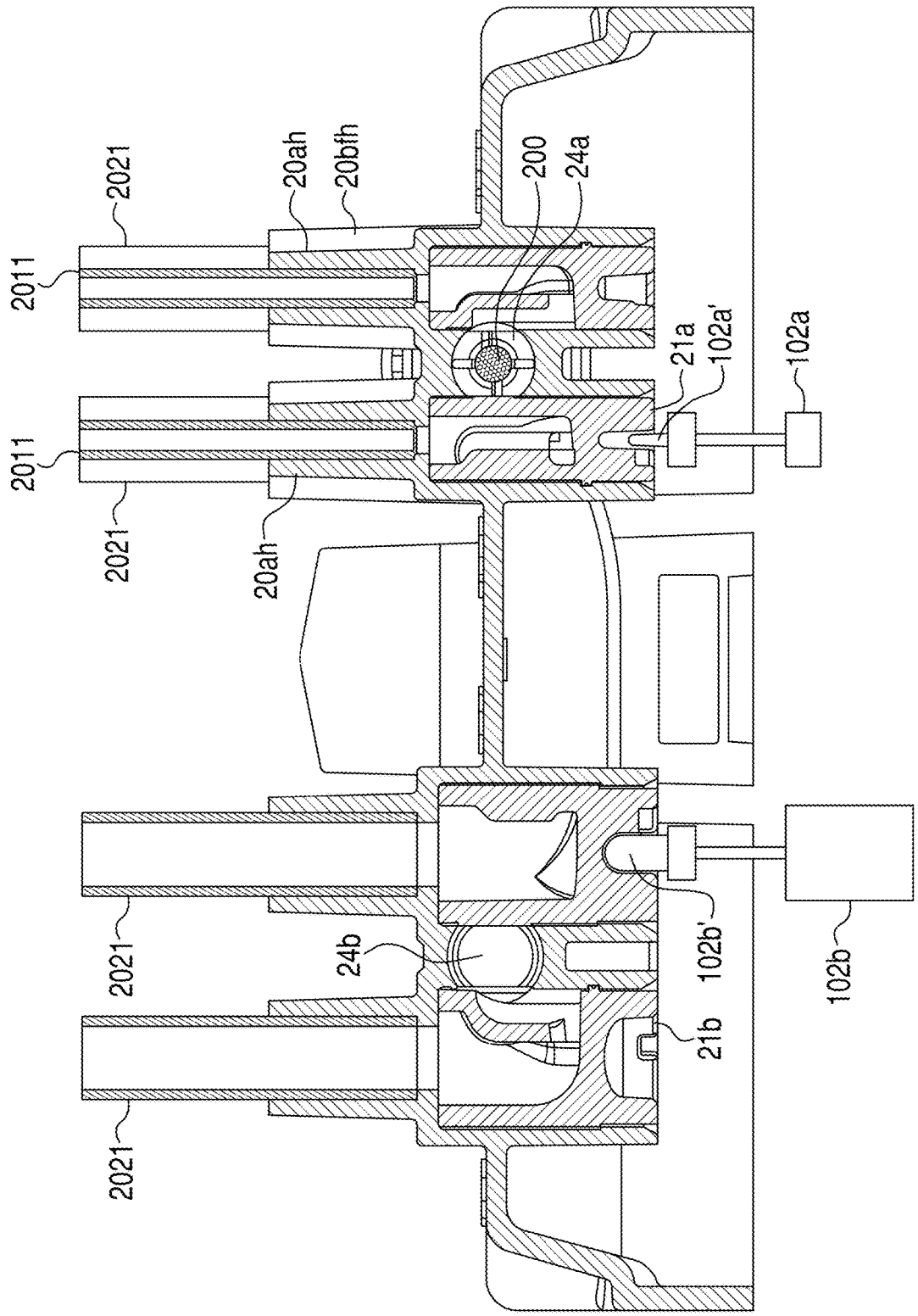
FIG. 9 is a cross-sectional view of two exemplary micro valves and two macro valves in open and closed positions and located in a valve housing in the manifold of FIG. 1.

FIGS. 7C and 9 show the valves 21a, 21b and filler 200 in place in the manifold 20. The filler 200 takes up volume within the first channel 24a such that the cross sectional area of the first channel 24a taken normal to a longitudinal axis of the channel 24a is smaller than the cross sectional area of the second channel 24b taken normal to a longitudinal axis of the channel 24b. Thus, the inner periphery of the first channel 24a and second channel 24b can be similarly shaped, allowing for certain architectural benefits in placement of the valves 21a, 21b and in fluid flow geometry of the channels 24a, 24b. The filler 200 can include a filler rod 201 that includes a plurality of spacers 202 located along the rod 201 so as to keep the rod 201 centered within the channel 24a. A clip lock 203 can be provided at a proximal location of the rod 201 and configured to lock with a mating clip lock indent in the manifold 20. In particular, a flexible tab 203a can be located on the lock 203 and configured to mate and lock with opening 203b in manifold 20 (See FIG. 7C). A sealing member 204, such as an O-ring 204, as shown in FIG. 7B, can seal the filler 200 in the socket 26 to prevent fluid such as air or liquids from leaking into or out of the channel 24a via the socket 26 when the filler 200 is located therein. The sealing member 204 can be located in an indent or receiving groove 204a on the rod 201 to lock the sealing member 204 in place with respect to the filler 200. One function of the filler 200 is to reduce common volume in channel 24a, which reduces priming volume and flushing volume. Because the micro pump only achieves limited flowrates, the large cross section of channel 24a without the filler would be difficult to be flushed of residuals.

Placement of the filler 200 in the channel 24a has the added benefit of increasing (or otherwise controlling and directing) turbulence within the channel 24a, and thus increases maximum fluid velocity within the channel 24a, permitting faster and more thorough flushing of residual fluids in the channel 24a to output 25a. The filler 200 can be conveniently loaded into the manifold via socket 26 during the time the manifold assembly 20 is being manufactured. The filler 200 geometry, particularly at the downstream end, is designed to promote flushing and to avoid areas where residual fluid can hide out and not flush properly.

Figure 8A:
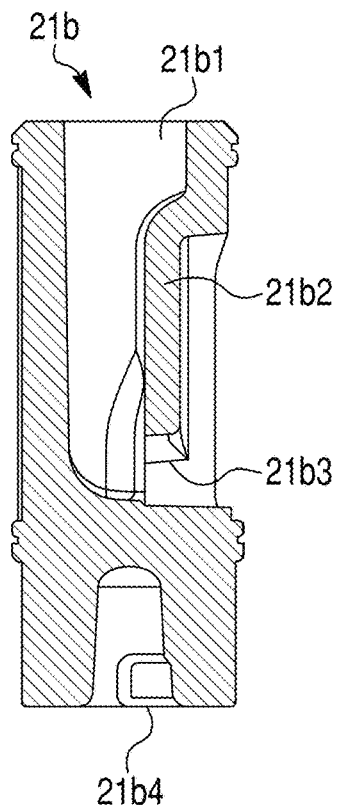
FIG. 8A is a cross-section taken along line 8A-8A of FIG. 8B.
Figure 8B:
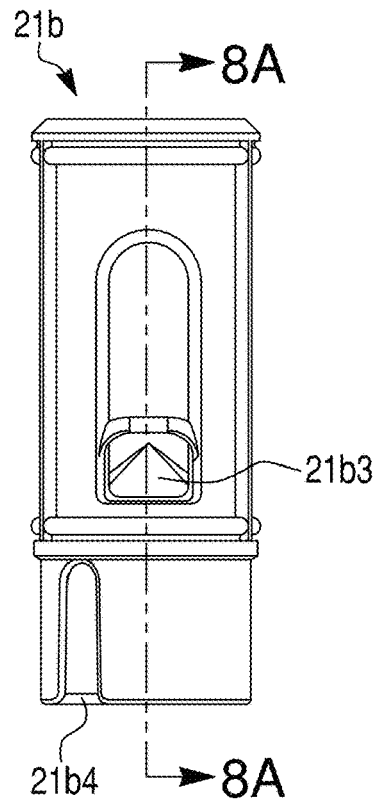
FIG. 8B is a side view of the valve shown in FIG. 7B.

Each of the micro and macro valves 21a and 21b can be configured as a rotational type valve that, when rotated a set amount, permits a corresponding or known amount of fluid to bypass the valve. In one embodiment, the valves 21a, 21b can be configured such that rotation of each of the valves does not move fluid, and only opens/closes a fluid path. The amount of fluid that bypasses the valve can, however, be ultimately determined by the pump speed, size and in conjunction with the tubing size when using a peristaltic pump. The valves can be configured to simply open or close the fluid lines. FIG. 8A shows a macro valve 21b that includes an inlet 21b1 at a top of the structure and an outlet 21b3 at a side wall of the structure. Thus, fluid enters the top of the valve 21b along a rotational axis of the valve 21b, and exits a side of the valve 21b in a direction substantially normal to the rotational axis of the valve 21b. Rotation of the valve 21b is accomplished by connection to a stepper motor 102b via actuator connection slot 21b4 located in a bottom surface of the valve 21b. The slot 21b4 acts as a keyway for a corresponding projection 102b' extending from the top of the stepper motor 102b. When the stepper motor 102b turns the projection 102b' a preset amount, the valve 21b is also caused to turn the same amount due to the connection between the projection 102b' and the keyway or slot 21b4. When the valve 21b is located in an open position or a semi open position, fluid can travel from the inlet 21b1 down through a center of the valve 21b until it passes wall 21b2, which can be configured as a gravity wall, or P-Trap, or similar structure. After passing the wall 21b2, the fluid then changes directions by approximately 180 degrees and moves up and over the outlet wall in the manifold 20 to be distributed into the second channel 24b. The wall 21b2 and geometry and configuration of surrounding manifold walls prevents fluid from inadvertent and uncontrolled mixing between lines 2011/2021 and the common volume of channel 24a on the micro side and between lines 2011 and the common volume of channel 24b on the macro side when 1) the valve is open, 2) the fluid is static (i.e., pump rotors 41 and 42 are not moving), and 3) there exists a differential in specific gravity between the respective fluids in the input lines and in the channels. The motivator for this backflow is specific gravity differences between the ingredient fluid and the fluid in the channel. This wall 21b2 is a technical feature of the valve that mechanically prevents this backflow from occurring without additional control mitigations, and requires no additional software/valve controls to limit the effect of this backflow tendency because the wall structure physically stops or prevents backflow from happening. Thus, the walls 21b2 and surrounding geometry of the valve housing 21bh prevents contamination of the ingredients in the supply lines and storage containers 4b and prevents uncontrollable flow/mixing into the channels 24a and 24b of the manifold 20 due to, for example, differences in specific gravity of the solutions or fluids running through the valves. The output of the micro and macro valves 21a, 21b (with respect to each respective opening into the common channels 24a, 24b located in manifold 20, shown in FIG. 9) is above the above-described "P-trap" thus not allowing flow that might otherwise enter into the manifold 20 due to specific gravity differences. Thus, the valves 21a, 21b work with the structure of the manifold 20 in this embodiment to form the specific gravity "P-trap" structures.

Although FIGS. 8A and B show a macro valve 21b, the micro valve 21a can be configured and will operate in the same manner, albeit using smaller dimensions.

The two motors that drive each of the rotors 41, 42 can be the same, and similarly the rotors 41, 42 can be identical. The tubing in each channel can be different, and the platen positions can be different because of the difference in the diameter and wall thickness of the tube sections.

Figure 10:
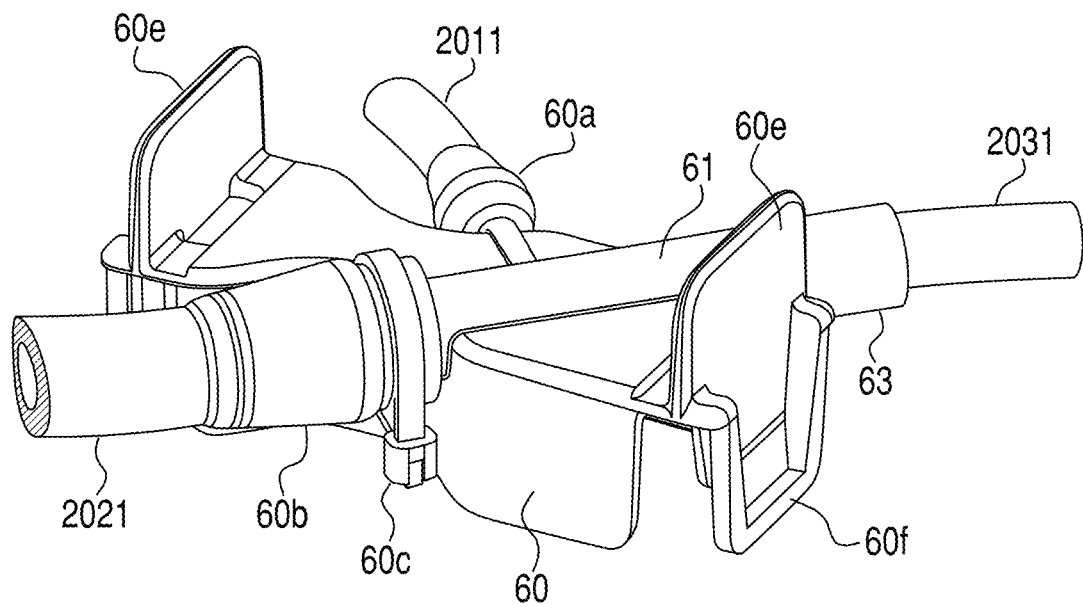
FIG. 10 is a top perspective view of an exemplary union junction.

FIG. 10 shows a perspective view of the union junction 60. The union junction 60 is configured to retain and/or receive a tubing structure that includes a micro input line inlet port 60a, a macro input line inlet port 60b, a union junction line 61 and an outlet port 63. The micro input line inlet port 60a is configured to receive the micro line 2011 which carries fluid from the micro channel, which can include fluid from one or both the micro fluid containers and macro fluid containers that were described earlier. The macro input line inlet port 60b is configured to receive the macro line 2021 which carries fluid from the macro fluid containers that were described earlier. The micro input line inlet port 60a and the macro input line inlet port 60b are both coupled to a junction line 61. Thus, fluid flowing from the micro line 2011 enters the micro input line inlet port 60a and flows through the junction line 61 and is combined with fluid received by the junction line 61 from the macro line 2021 via the macro line inlet port 60b. In this manner, fluid from micro line 2011 is combined with fluid from the macro line 2021 for delivery to the receiving/final container (e.g., IV bag 80). FIG. 10 also shows macro input line tie down 60c that maintains the macro input line inlet port 60b in place. A similar tie down 60c can be used to secure or maintain the micro input line inlet port 60a in place. The junction line 61 includes an outlet port 63 coupled to a combined fluid line 2031. As fluids from the micro line 2011 and the macro line 2021 combine in the junction line 61, they flow through the outlet port 63 to the combined fluid line 2031. The fluid flows from the combined fluid line 2031 to the final container or receiving bag filling station which is described in greater detail below. FIG. 10 also shows that the union junction 60 includes handles 60e which can be used for the placement and removal of the union junction 60 onto mating receptacles on the housing 10. Locks, such as flexible spring locks 60f, can mate with receptacles on the housing 10 to further secure the junction 60 thereto.

Figure 11:
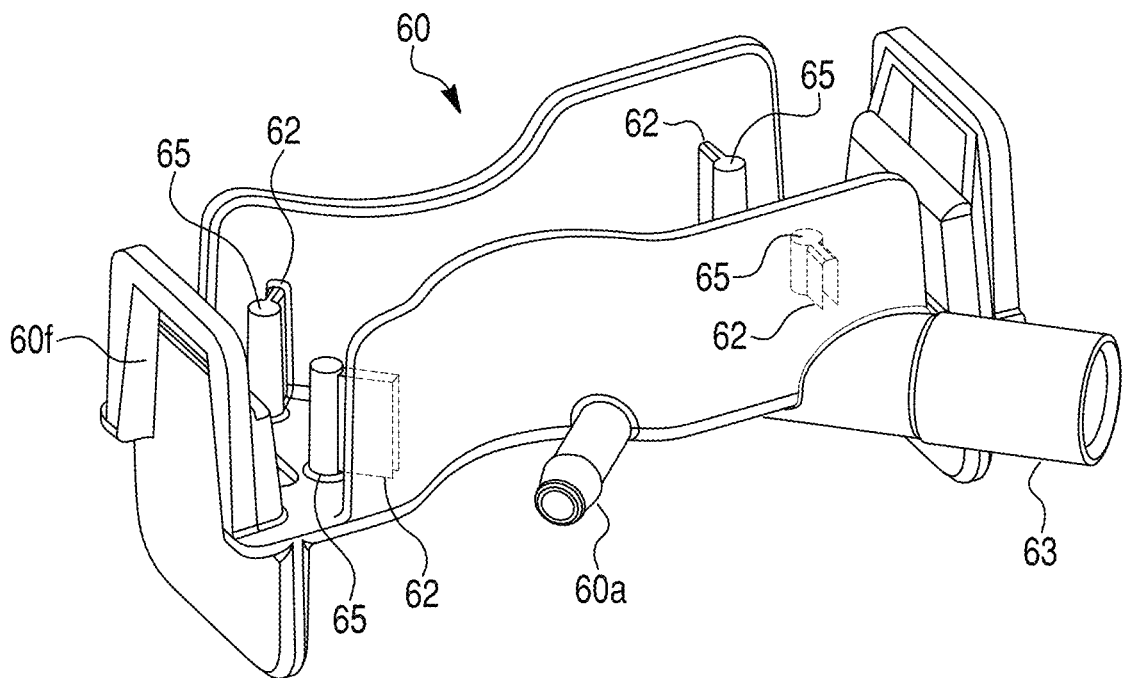
FIG. 11 is a bottom perspective view of the exemplary union junction of FIG. 10.

FIG. 11 shows a bottom side perspective view of the union junction 60. FIG. 11 shows that the union junction 60 includes a plurality of standoff ribs 62 and pin bosses 65 which are spaced apart from each other along an interior surface of the union junction 60. The standoff ribs 62 and pin bosses 65 are configured to provide an insertion spacing stop to retain the junction 60 at a predetermined distance/height relative to the housing surface. The standoff ribs 62 and pin bosses 65 can also provide structural integrity for the tubing structures described above, including the micro input line inlet port 60a, the macro input line inlet port 60b, the junction line 61 and the outlet port 63 so that those structures are maintained in place even as fluids are passed therethrough.

Figure 12:
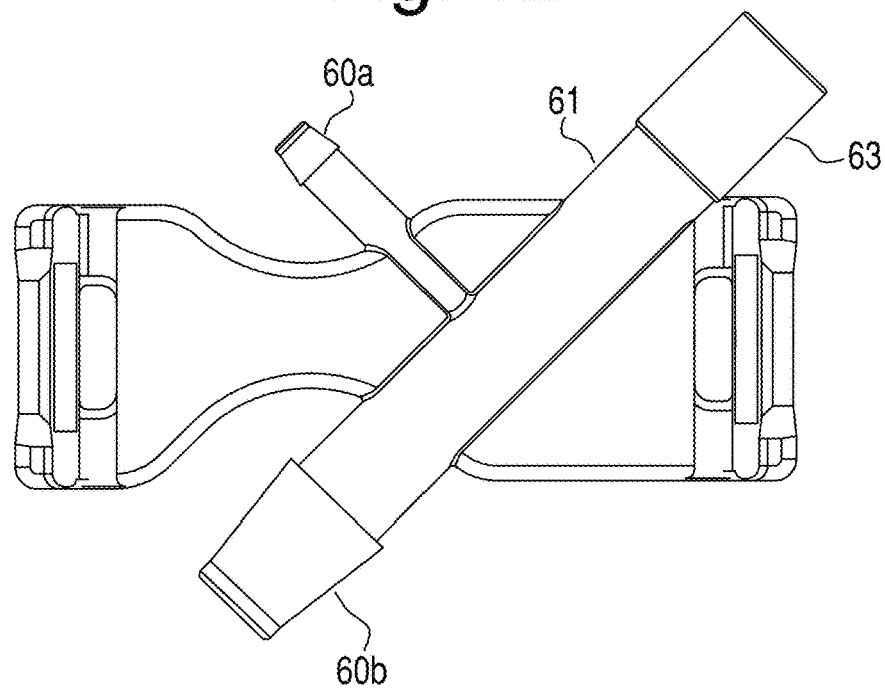
FIG. 12 is a top view of the exemplary union junction of FIG. 10.

FIG. 12 shows a top view of the union junction 60 with the tubing structures described above in place. As can be seen in FIG. 12, the union junction line 61 receives fluid via the micro input line inlet port 60a and the macro input line inlet port 60b. The fluids mix in the union junction line 61 and are carried to the outlet port 63 for eventual delivery to the receiving bag 80. As shown in the FIG. 12 and in this exemplary embodiment, the micro input line inlet port 60a joins the union junction line 61 in a direction perpendicular to a longitudinal direction of the union junction line 61, while the macro input line inlet port 60b causes fluid to flow into the union junction line 61 in the same direction as the longitudinal axis of the union junction line 61. In alternative embodiments, the micro input line inlet port 60a can join the union junction line 61 at any angle relative to the longitudinal direction of the union junction line 61 so as to optimize usability of loading onto the platform 10d and notch 18 and simultaneously ensure proper contact with pump rotors 41, 42 and optimize flushability of the union junction 61.

The tubing structure described above, including the micro line inlet port 60a, the macro line inlet port 60b, the union junction line 61 and the outlet port 63 can be formed, e.g., molded, into the union junction 60 so as to form a unitary structure. Alternately, the tubing structure can be formed as a separate unit that can be placed or snapped into the union junction 60 and retained in place using a mechanism such as the standoff ribs 62 and pin bosses 65 described above. In addition, it should be understood that the compounding device 1 can be configured without the presence of a union junction 60 as shown. Instead, the union structure can be the final container, such as the receiving bag 80 itself. For example, lines 2011 and 2021 can extend about rotors 41, 42 and continue all the way to two separate ports in the receiving bag 80 such that mixing of materials from lines 2011 and 2021 occurs only at the receiving bag 80. In this case, it may be beneficial, depending on the particular operating parameters, to secure lines 2011 and 2021 at locations downstream of the rotors 41, 42 to ensure proper and efficient operation of the pump 40.

Figure 13:
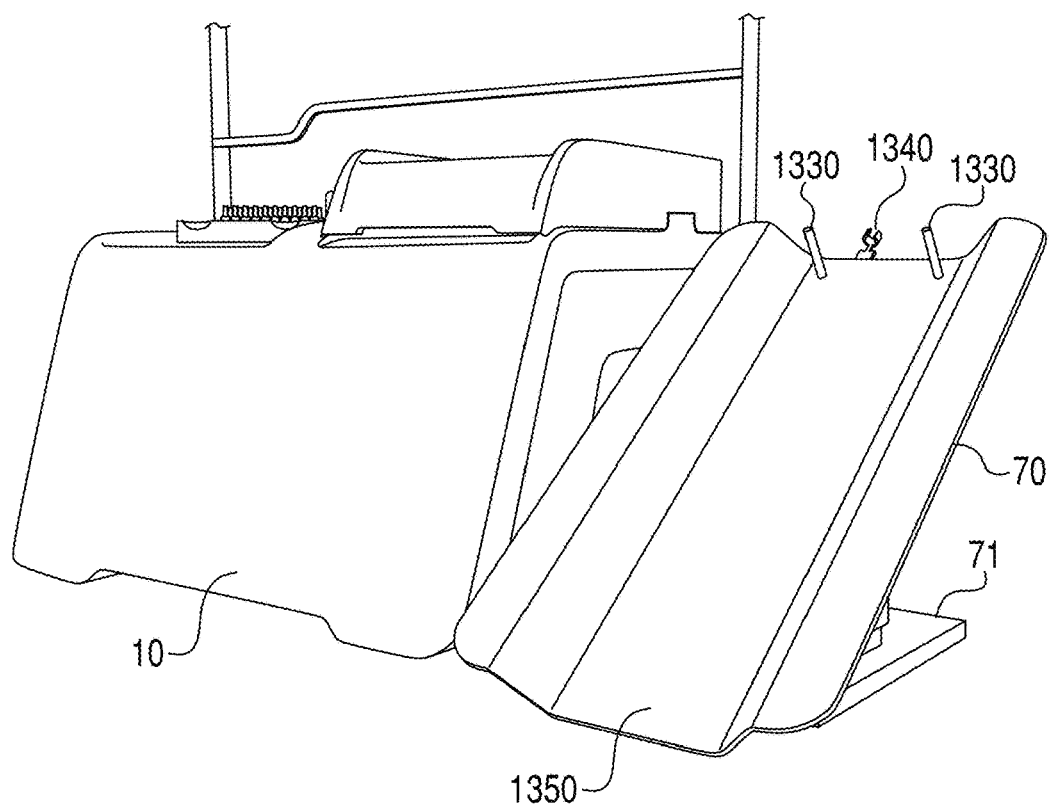
FIG. 13 is a partial perspective view of a compounding system made in accordance with principles of the presently disclosed subject matter.

FIG. 13 shows perspective view of the compounding system 1 in accordance with an exemplary embodiment. FIG. 13 shows housing 10 located adjacent a bag tray 70 for holding a receiving bag 80 during the filling process. A load cell 71 or other device, such as an analytical balance, can be integrated into the bag tray 70 to provide information relative to the weight and contents and to facilitate calibration as well as confirmation of operational functions for the compounding device 1. Protective devices and/or software can be incorporated into the device to protect the load cell 71 or other measuring device from damage due to accidental overload or other mishaps. As shown in FIG. 13, the bag tray 70 includes a bag tray receiving section 1350 that accommodates the shape of the receiving bag 80. The bag receiving section 1350 can be formed as a generally indented surface within the surface of the bag tray 70. The bag tray 70 also includes bag tray pins 1330 which are formed on an upper section of the bag tray 70. As shown in FIG. 13, the bag tray pins 1330 are formed perpendicular to the surface of the bag tray 70 so as to project in a direction away from the top surface of the bag tray 70. The bag tray pins 1330 are positioned to receive and hold a receiving bag 80 for filling. FIG. 13 also shows a bag tray clip 1340 which is formed along an upper section of the bag tray 70. The bag tray clip 1340 can be configured to keep a known tubing artifact constant with respect to the fluid line(s) 2031 connected to the receiving bag 80 (i.e., can be configured to dampen vibration or other force transmission to the bag 80 and/or load cell 71). Depending on how the bag 80 is connected to the outlet of the transfer set, and how the tube is positioned, variances can occur. The clip 1340 prevents these variances.

Figure 14A:
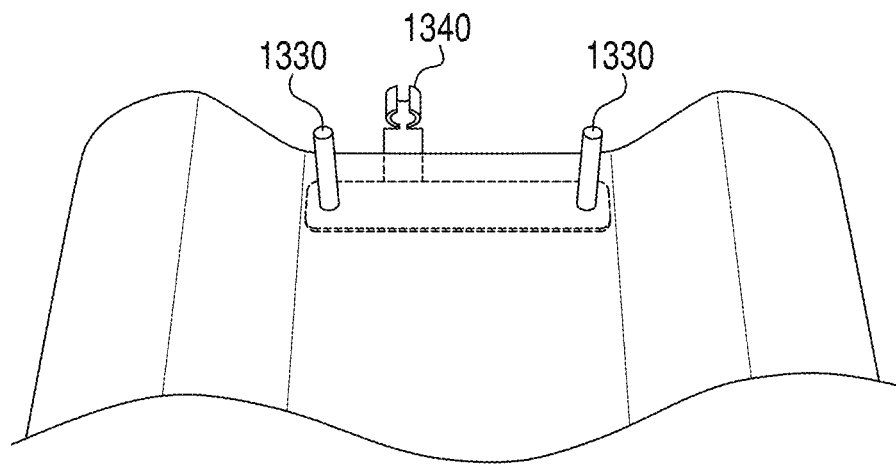
FIGS. 14A and 14B are partial perspective views of the bag tray and receiving bag.
Figure 14B:
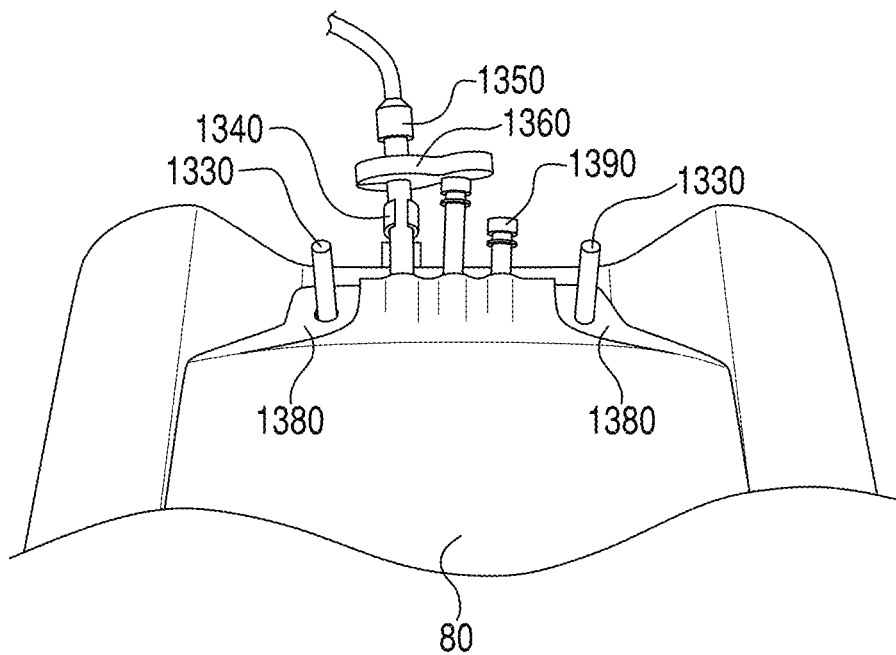

FIG. 14a shows a close up view the upper section of the bag tray 70 illustrating the placement of the bag tray pins 1330 that are positioned to receive and retain a receiving bag 80 for filling. FIG. 14a also shows the bag tray clip 1340 which is provided to secure the container input tubing, which includes the combined fluid line 2031. FIG. 14b shows a close up view of the upper section of the bag tray 70 including a receiving bag 80 placed in the bag tray 70. The exemplary receiving bag 80 includes two openings 1380 for receiving the bag tray pins 1330. Thus, when the bag tray pins 1330 are placed through respective openings 1380 of the receiving bag 80, the receiving bag 80 is maintained in place for filling. FIG. 14b also shows a twist lock 1350 formed on the end of the combined fluid line 2031. The twist lock 1350 is configured to connect to and lock with a port 1360 formed on a top surface of the receiving bag 80. The twist lock 1350 allows the combined fluid line 2031 to be securely coupled to the receiving bag 80 so that the receiving bag 80 can be filled. The bag tray clip 1340 can be configured to securely retain the port 1360 and twist lock 1350 that allows for quick placement, filling and removal of the receiving bag 80. The clip 1340 also secures the tubing to the bag tray to prevent unwanted artifacts in the load cell 71 measurement that could occur from excessive motion of the tubing segment that spans the gap between the bag tray and the pump module. This tubing motion could be caused by user interaction or pump vibration during compounding. Manual port 1390 can be provided at the top of the receiving bag 80 such that a user can inject an ingredient that is either not included in the compounding system 1 or has run out and is required to complete the receiving bag 80.

In similar fashion to the description above, a dual chamber bag may be filled using a slightly modified workflow, wherein the dual chamber bag keeps incompatible ingredients separate by two physical separated chambers that are kept separate from each other during compounding, but are combined just before infusion of the patient is started. All of the steps described above are followed for the 'primary' side of the receiving bag. Once complete on the primary side, the primary side port 1360a is disconnected from the twist lock 1350. The secondary bag port 1360b can then be connected to the twist lock 1350 and the secondary chamber thus filled.

Figure 15:
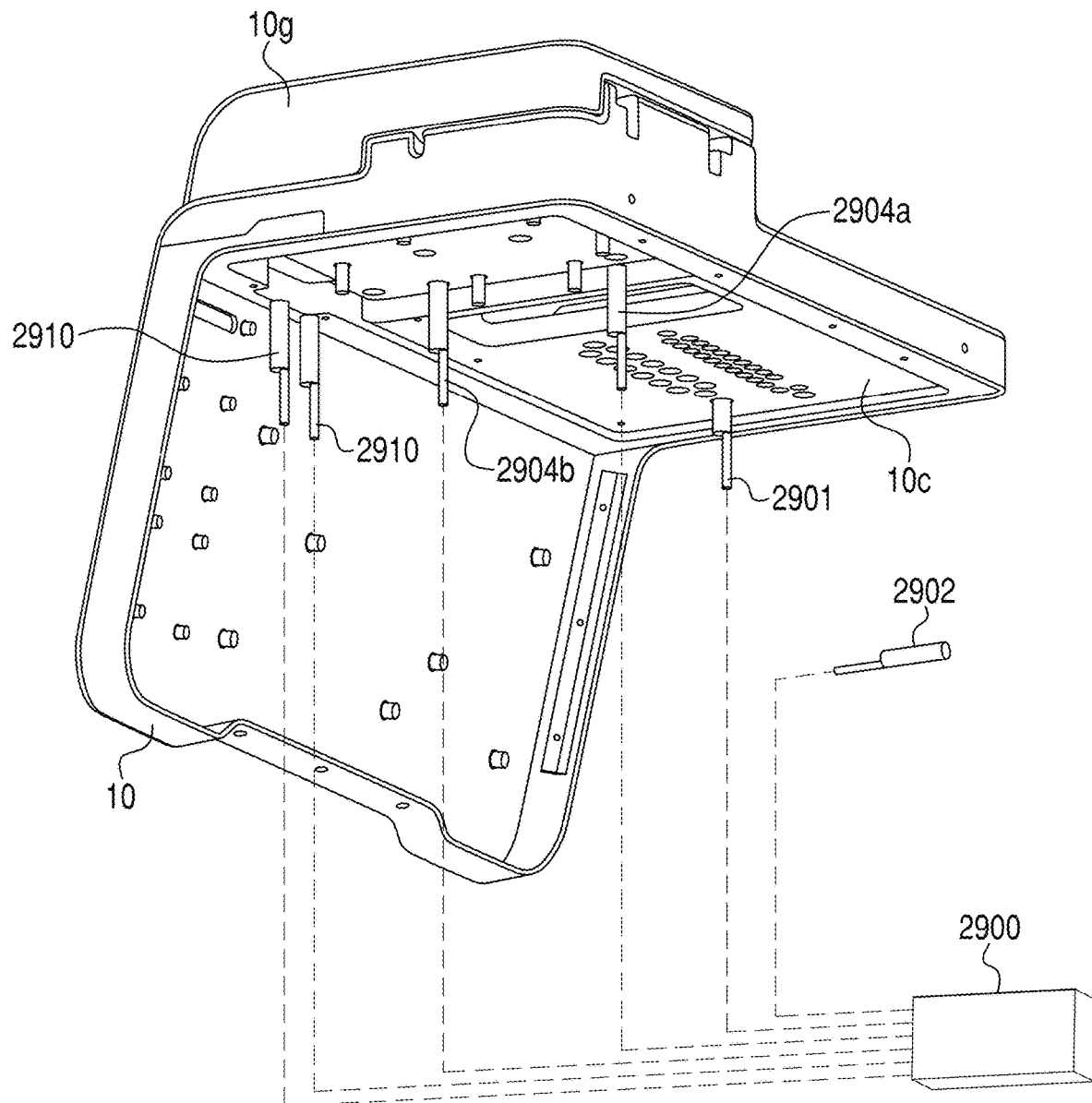
FIG. 15 is a right rear corner perspective view of a front/top panel and sensor array for the compounding system of FIG. 1.

FIG. 15 is a rear partial perspective view of the compounding system 1 that shows an exemplary sensor array used in conjunction with the system. Sensors 2910 can be configured to sense when the covers 10f and/or 10g are in place (See FIG. 3A). Alternatively, a reed switch sensor can be built into the combination sensor assembly to provide confirmation that 10f is closed. Sensors 2910 can be magnetic, such that they serve two purposes: 1) communication to a controller 2900 information indicating that the covers 10f and/or 10g are in a closed/operational position; and 2) securing, via magnetic force, the covers 10f and/or 10g in place in the closed/operational position. It should be understood that the sensors themselves may not provide enough force to provide a hold down function. Instead, a ferrous catch plate and lid magnet can be used in conjunction with the magnetic sensor. Sensors 2904a and 2904b can be configured to communicate to the controller 2900 that the platen locks 44a and 44b, respectively, are in a closed/operational position. Sensor 2901 can be provided in housing 10 and configured to communicate with the controller 2900 information that indicates that the manifold 20 has been properly affixed to the housing 10 and is ready for operation.

Sensor 2902 can be located adjacent a rear surface of the housing 10 and configured to communicate with the controller 2900 information that places the compounding system 1 in a service or firmware/programming mode when a maintenance operator or technician activates this sensor (for example, by placing a magnet adjacent the sensor 2902). The location of the sensor 2902 may be known only to service and technical maintenance personnel.

The exemplary compounding system 1 can also include a compounding control manager which resides in a central processing unit (e.g., controller 2900). The compounding control manager allows a clinician or other healthcare or compounding professional to enter, view, adjust and offload information pertaining to a given compounding protocol. In general, the compounding control manager is the program language that provides the operator with real time feedback and interaction with the compounding device through graphical user interface (GUI) elements. The GUI elements, created in a graphical format, display the various inputs and outputs generated by the compounding control manager and allow the user to input and adjust the information used by the compounding control manager to operate the compounding device. To develop the GUI elements, the compounding control manager can utilize certain third party, off-the-shelf components and tools. Once developed, the compounding control manager can reside as a standard software program on a memory device.

The controller 2900 can include firmware that provides several adjustment algorithms or hardware solutions to control the accuracy of the pump 40. For example, the pump output can be corrected for wear of the pump tubing lines 2011, 2021 over the life of the transfer set or manifold 20. This adjustment is applied as a function of the number of pump rotations experienced by each tubing line. The controller 2900 can also include software or hardware such that pump output or "flow factor" can also be adjusted for the specific fluid being pumped. This "flow factor" can account for fluid viscosity, pump speed, line type, and source container/spike type. The controller 2900 can also be configured to correct pump output for the rotational location of the pump rotor 41, 42 rollers relative to the platens 43a, 43b. This adjustment can be significant for small volumes that are dispensed and which represent only a few rotations of the pump head or less. Note that absolute encoders can be included on both pump motors 41s, 42s (and valve steppers) to provide the firmware (e.g., controller 2900) with the information necessary to make the above-noted adjustment(s). The controller 2900 can include a bubble detection algorithm that attempts to minimize nuisance alarms.

FIGS. 16-34 are a walk-through of display screens generated by a representative embodiment of the compounding control manager, which demonstrate various features of the compounding control manager. After an initial start-up mode of software initialization, a main work area is created on a display device, which initially opens a log-in screen. The operator first identifies him or herself, either by using the bar code scanner to scan an operator badge number, or by entry of a badge number or other selected form of identification on the graphical touch screen entry pad. This identification procedure is required for logging-in and/or assessing the operator's level of security clearance. Desirably, a system administrator would have previously established a list of authorized users, against which the sign-in data is compared.

Figure 16:
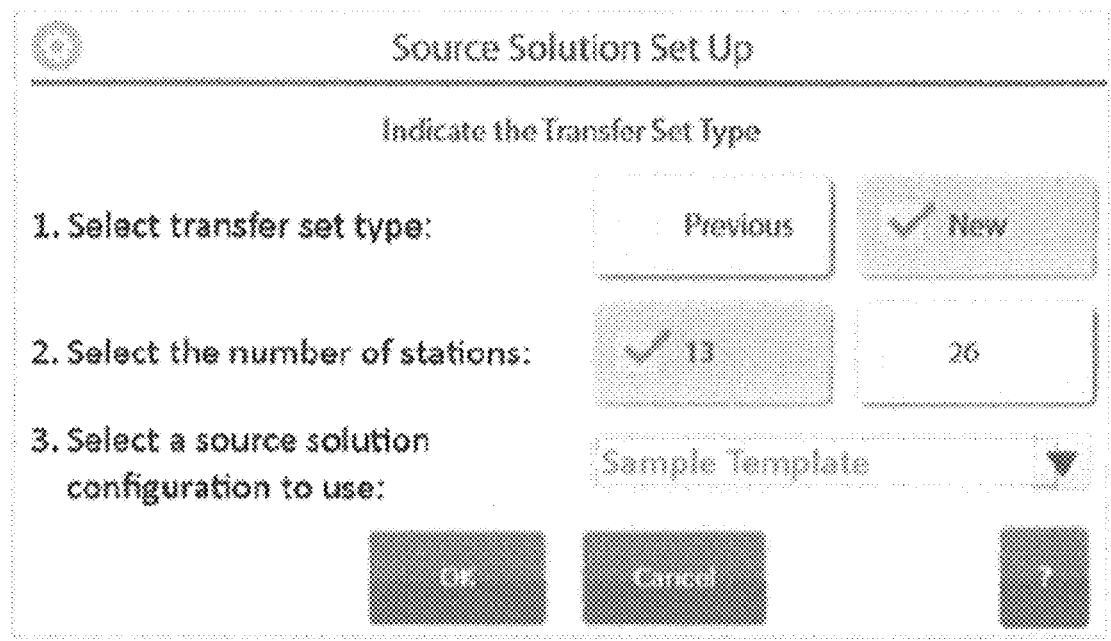
Figure 17:
Figure 18:
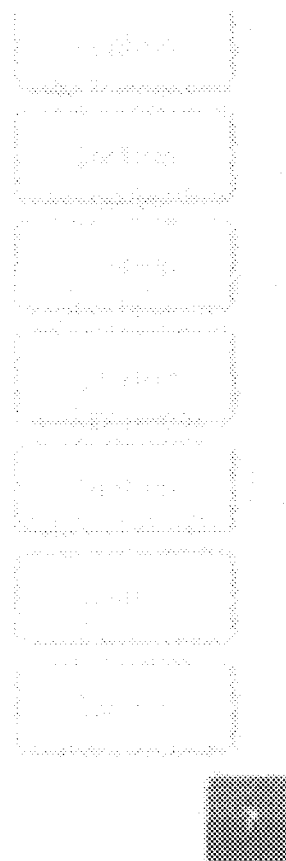

FIG. 16 depicts an interface that may be presented to a user after the user has logged in and been authenticated as an authorized user. FIG. 16 is a control panel that allows the user to indicate the type of transfer set to be used, select the number of stations to be used and select the source solution configuration template. The user may then be presented with the interface shown in FIG. 17. The interface of FIG. 17 allows the user to scan a bar code located on a lid of a tray in which the transfer set 2 is provided. In this manner, the system knows the transfer set 2 that the user has chosen. The user can then remove the transfer set 2 from the packaging and install it. The process of installing the transfer set 2 includes opening the device doors and platens, placing and snapping the transfer set manifold 20 to the top of valve actuators 102a', 102b' and platform 10c and draping the leads of the transfer set over a rack that is disposed in the laminar flow hood.

After the user snaps down the manifold 20 onto the device, the user may then route the tubing through a bubble and occlusion sensor followed by closing the sensor lid. Next, the user can route the tubing around the pump rotors and secure union junction to the pump module. Each of the rotors can include a bottom flange or guide member, 410, 420 that is configured to prevent the tubing from being installed too low or slipping or being pinched between the pump surface and the rotor. Finally, the user can close the platen locks and then close the pump door or cover. The user is also presented with the interface of FIG. 18 which includes a checklist of each of the tasks described above. Once each of the tasks is completed, the user can select "OK" to verify completion of the tasks. In this manner, the system ensures that the user has completed the transfer set installation before proceeding to the next step.

Figure 19:
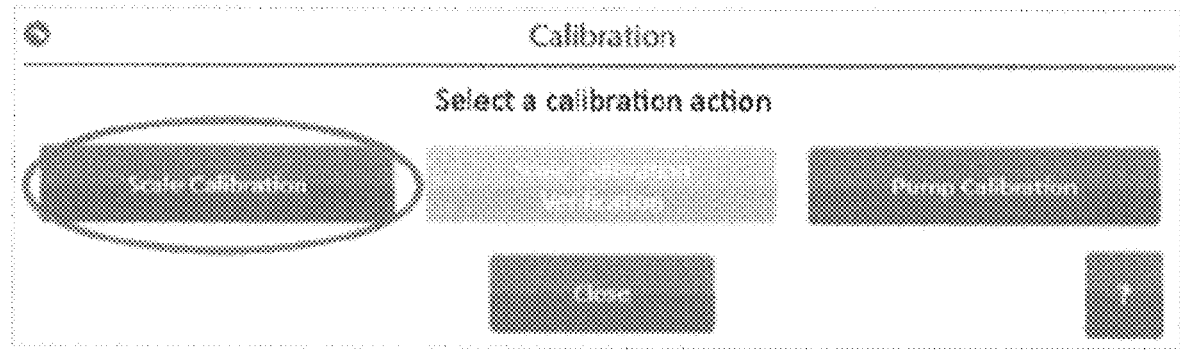
Figure 20:
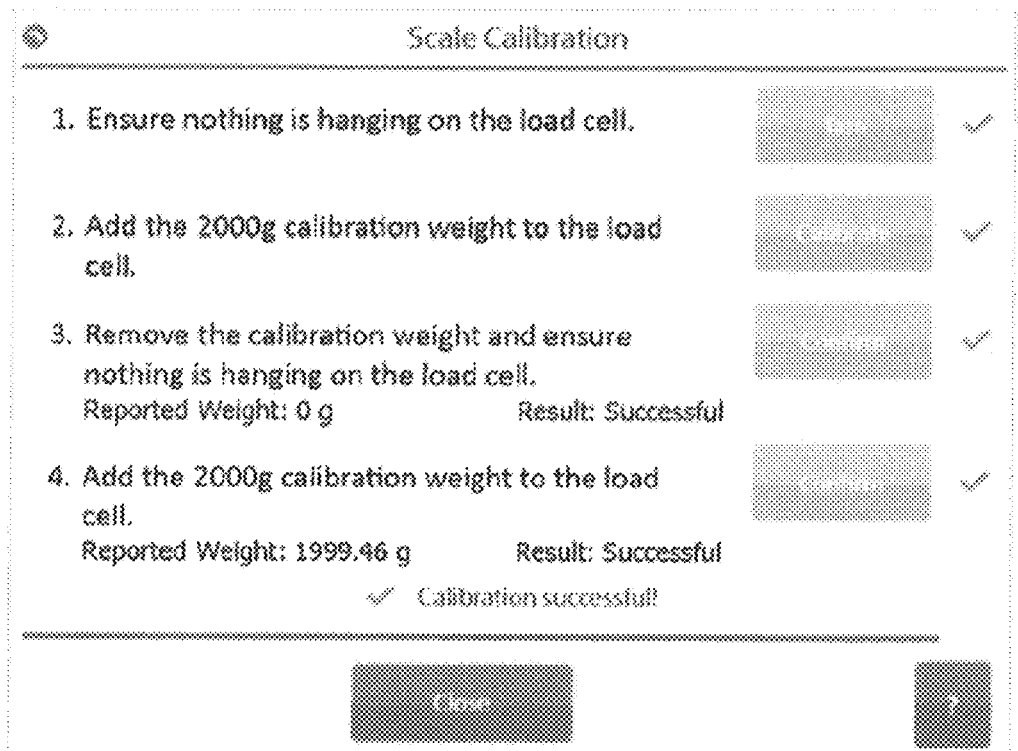

The user can then initiate calibration of the load cell 71 by selecting the "scale calibration button" shown in FIG. 19. FIG. 20 shows a further interface that is presented to the user to ensure that the load cell 71 is properly calibrated. When the calibration is completed, the user can then select the "close" button.

Figure 21:
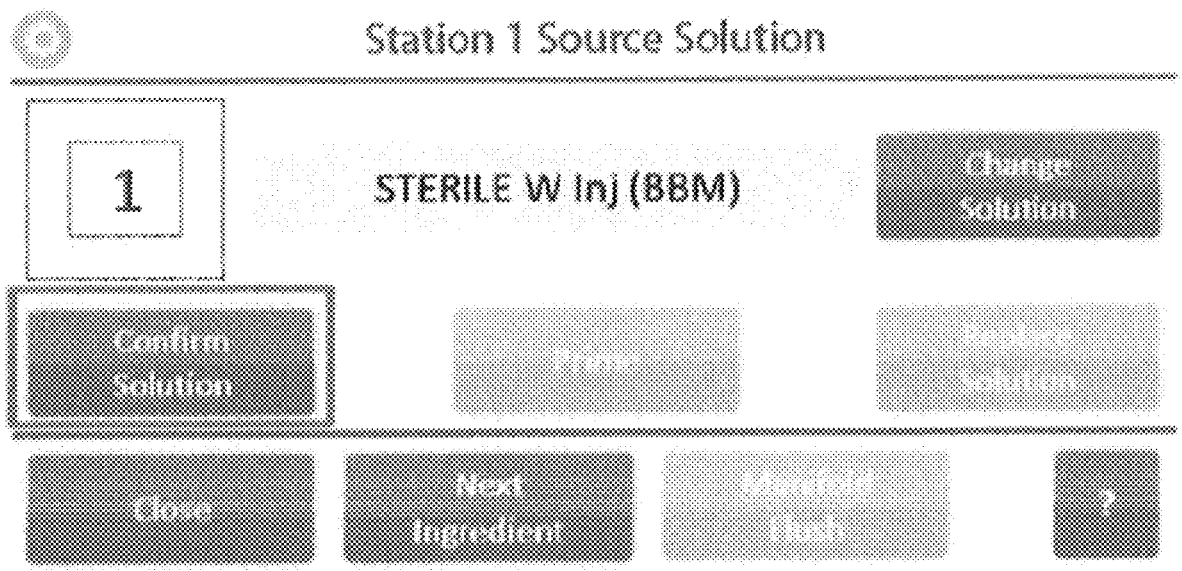
Figure 22:
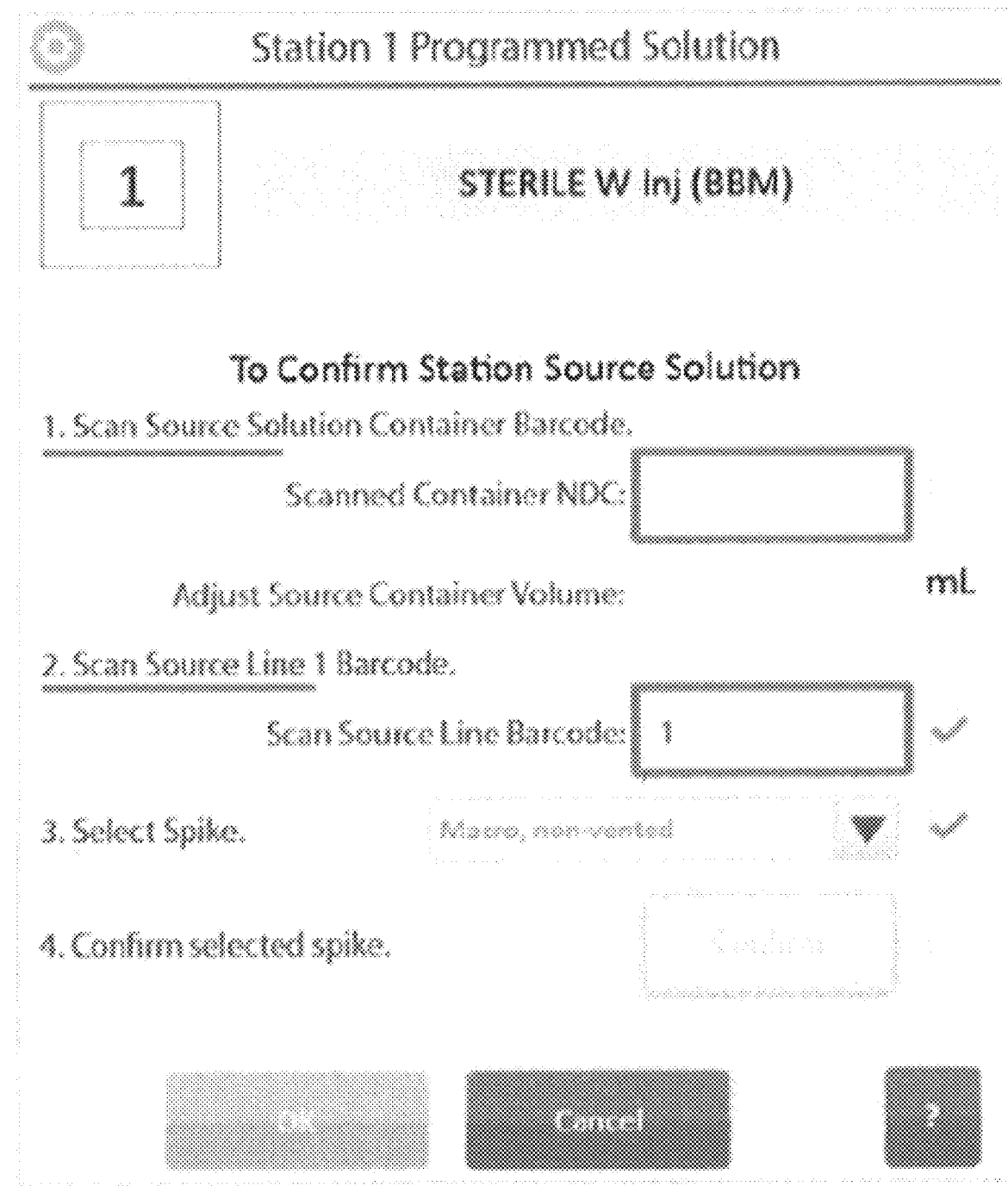

The user then confirms the source solutions. FIG. 21 shows an interface that is presented to the user for confirming the source solutions. The user can select the button that reads "confirm solution." At this point, the user can select the tubing lead (i.e., micro line 2011 or macro line 2021) to be confirmed and can remove a protective cap that covers the lead. The user can then attach the appropriate lead. The user can then attach the source container to the tubing lead and hang the container on the rack or rail. The user is then presented with the interface of FIG. 22 whereby the user can scan the bar code flag 802 of the tubing lead for the solution to be confirmed. The user can then scan the source container bar code 801 for the solution attached to the tubing lead that is scanned. The lot number and expiration date bar can also be scanned (FIG. 23).

Figures 23, 24:
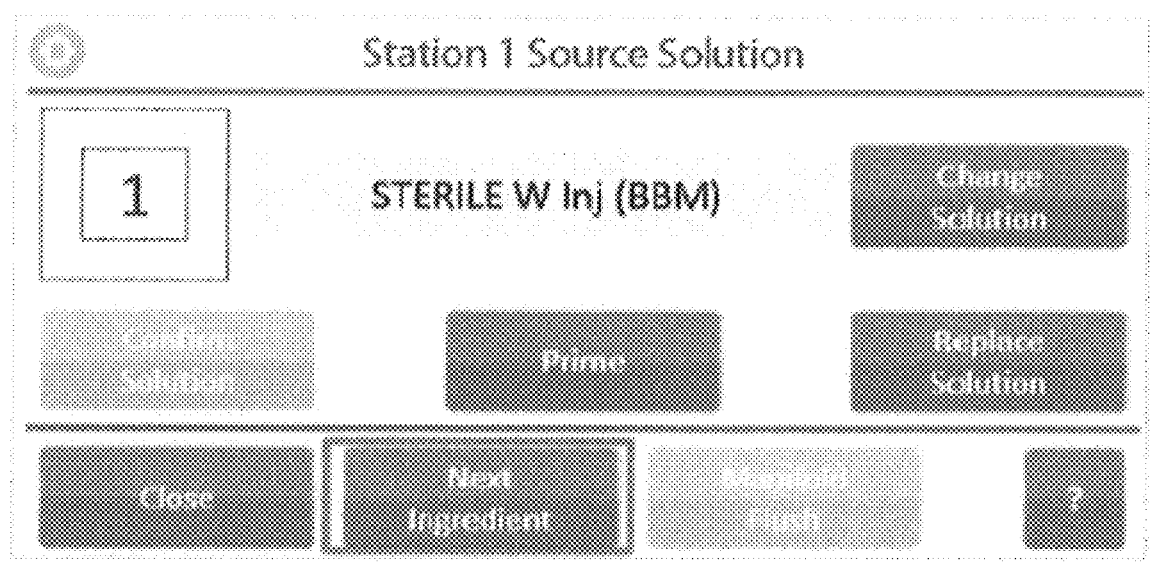
Figure 25:
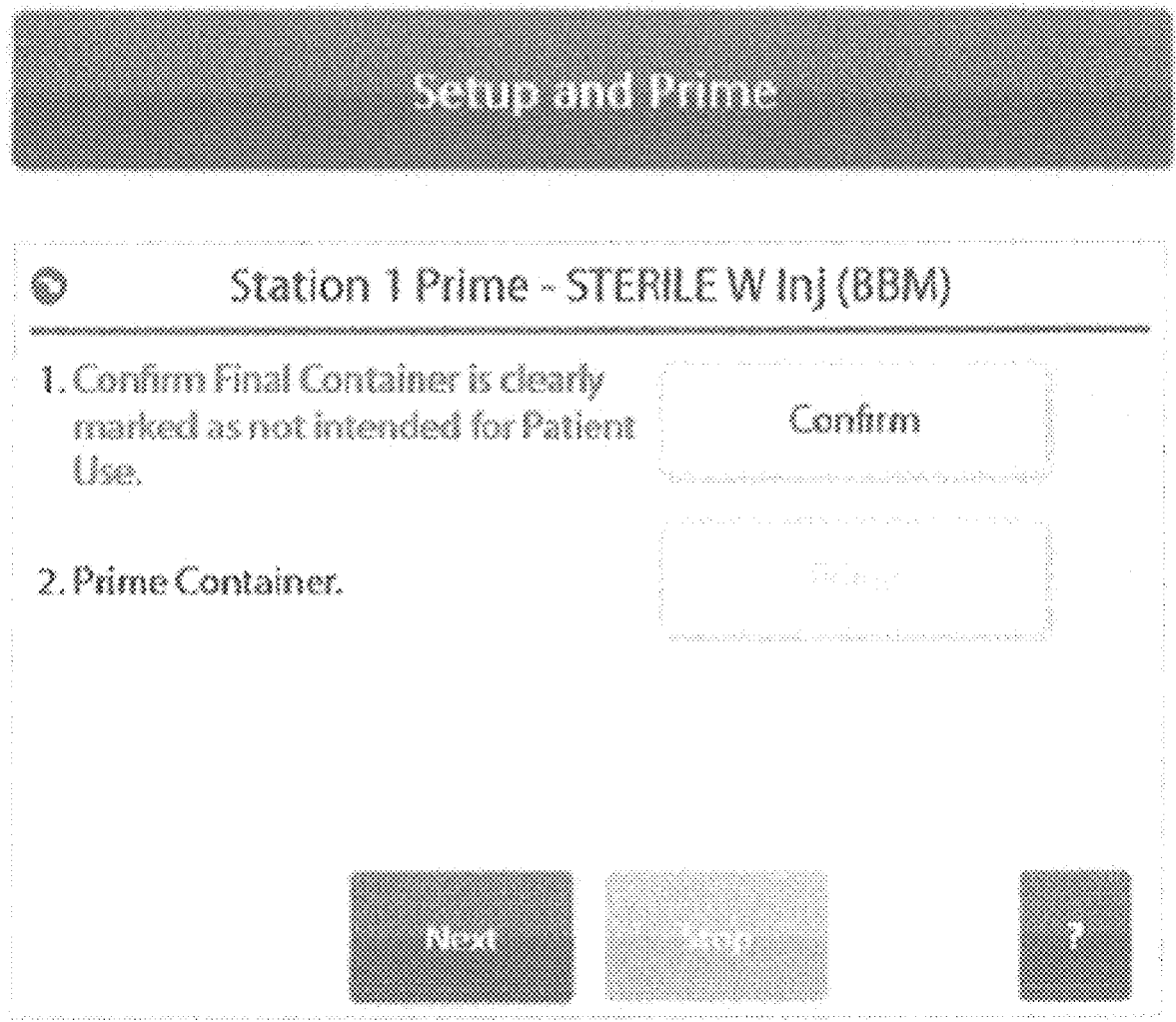
Figure 27:
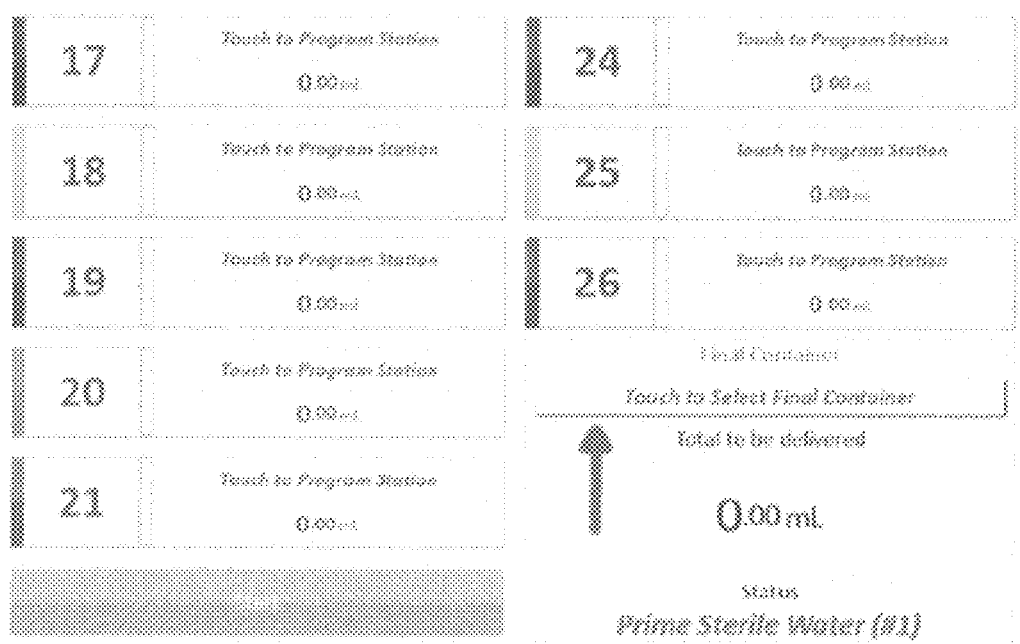
Figure 29:
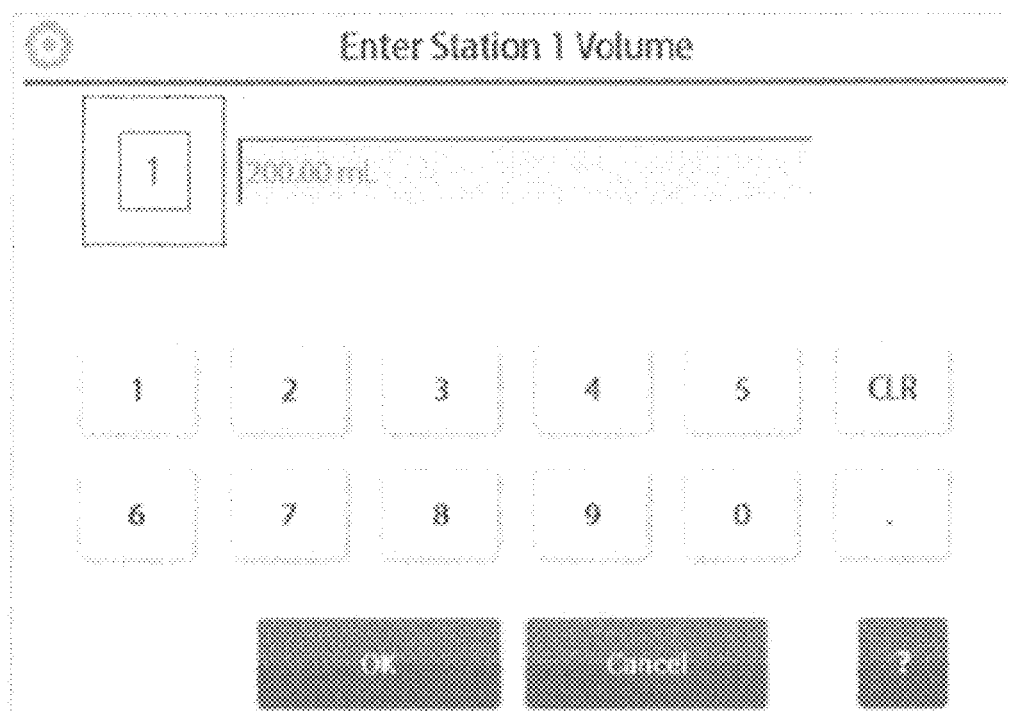
Figure 32:
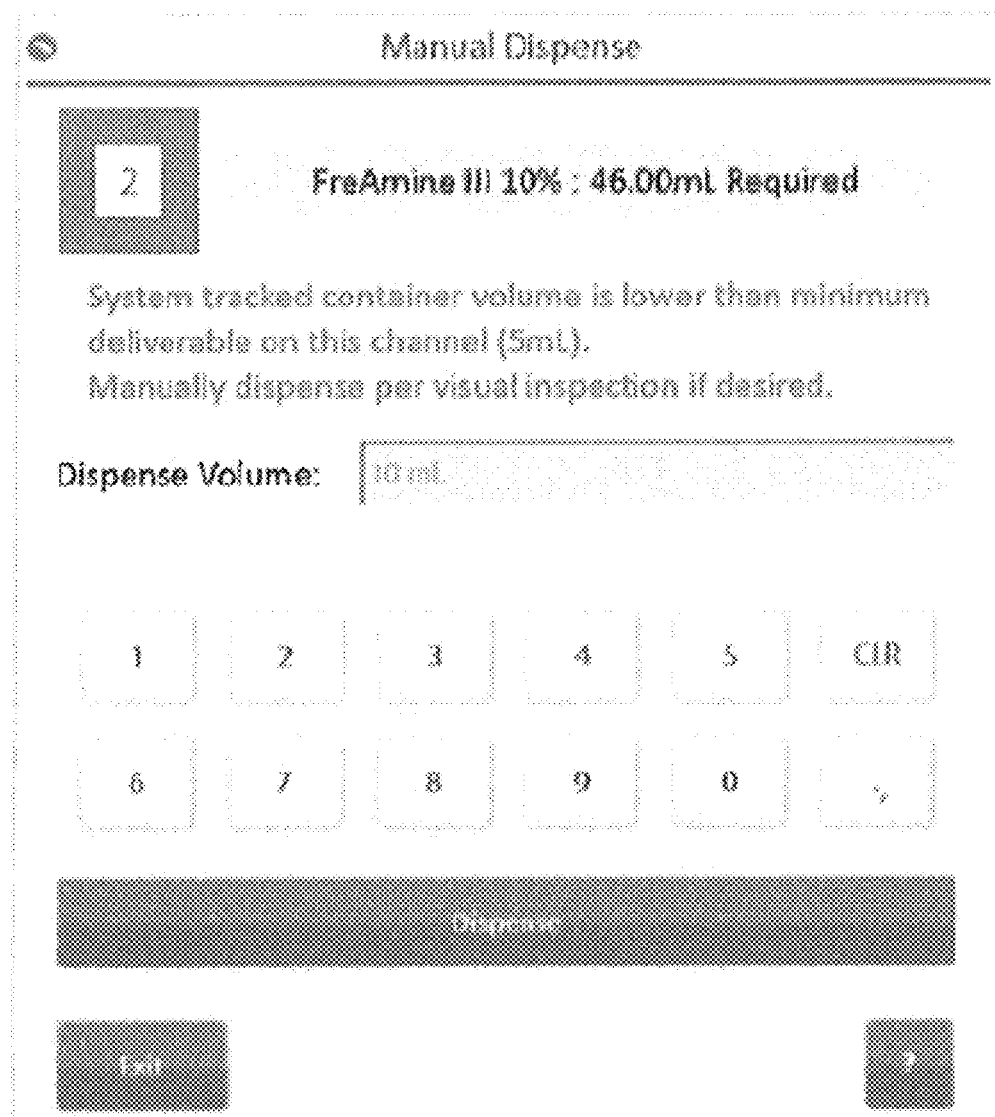
Figure 33:
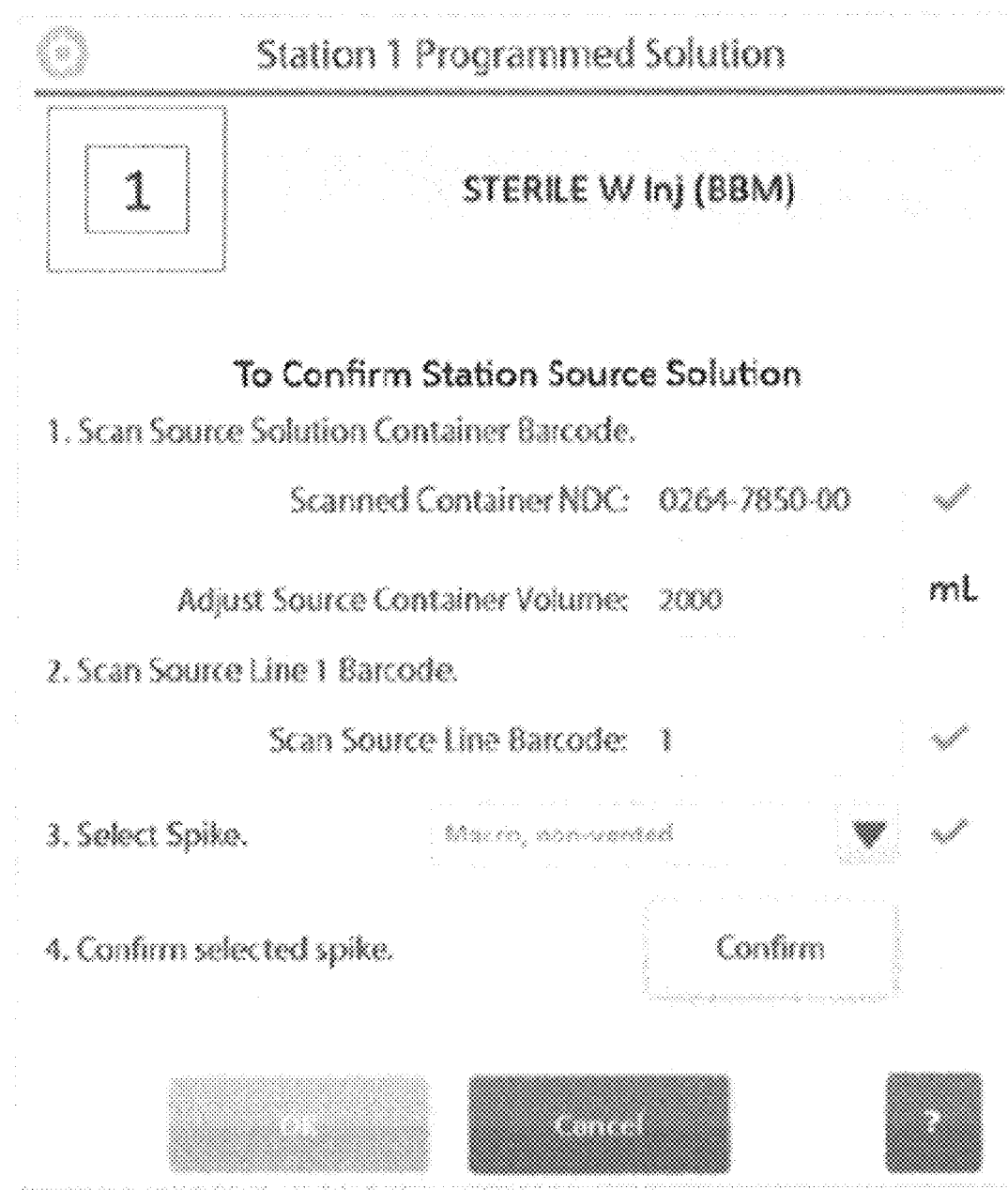

After completing confirmation of the first container, the user can select the "next ingredient" button shown on the interface of FIG. 24. This allows the user to repeat the steps of FIGS. 21-23 above which allows confirmation of all of the source solutions.

Once the source solutions have been confirmed, the user can initiate the priming of the solutions. The user first attaches a receiving bag 80, i.e., calibration container, to the load cell 71. Then, after all of the solutions have been confirmed, the user taps the "setup and prime" tab shown in FIG. 25. After priming is completed, the user can select the "next" button and repeat this process for all stations. The user can also initiate the manifold flush at this point. Next, the user can initiate a pump calibration sequence via the interface of FIG. 26. The user can then follow steps 1-5 of FIG. 26 to calibrate the pump. These steps include confirming that that calibration final container is attached and marked "Not for Patient Use"; calibrate the macro pump; confirm that the macro pump is calibrated; calibrate the micro pump; and then confirm the micro pump calibration. The user can then remove and discard the calibration bag.

Next, the user can install the final container (e.g., receiving bag 80). The user may be presented with the interface of FIG. 27 which allows the user to select the option of installing the final container. The user may then be presented with the interface of FIG. 28 which allows the user to select a single chamber or a dual chamber receiving bag. The user can then scan or enter the lot number and expiration date. The user can then attach the final container by removing the protective caps and attach the receiving bag 80 to the transfer set connector. The user can then install or otherwise attach the receiving bag 80 by using the hanging holes formed in the container to connect to the load cell pins and then attach the tubing inlet to the tubing clip.

At this stage, the system has been calibrated, the solutions to be dispensed have been verified and the receiving bag 80 has been installed and is ready to be filled. The user can manually program an order for the solutions to be dispensed using the interface shown in FIG. 29. Alternatively, the user can scan in an order or select an order from a transaction pending buffer (TPB) manager or a .PAT file. Utilizing the interface of FIG. 29, the user can enter all of the solution volumes to be dispensed. Once the solution volumes have all been programmed, the user can select the "start" tab shown in FIG. 30. As shown in FIG. 30, if a solution requires a source container 4a or 4b change while compounding the next formulation, the station will display the solution requiring a change in yellow.

The controller 2900 can be configured to review the prescription and to require the user to either change the sequence of the script or to add a buffer to avoid incompatibility issues in either of the common channels 24a, b (micro/macro). The pump 40 will control deliveries from each of the common channels by stopping one or more of the pumps 40 if the incompatible fluids would meet in the union connector 60 after the pumps 40.

FIG. 31 shows a warning interface that is presented to the user when the software determines that the source solution container 4a or 4b has insufficient volume. The user can then replace the container or, if there is some solution remaining, a manual dispense can be performed. If the user chooses to perform a manual dispense, the user enters the estimated volume remaining using the interface of FIG. 32.

In order to replace the solution, the user can remove the empty container 4a or 4b and place a new container on the tubing lead and hang. The user can then access the interface of FIG. 33 to scan the bar code flag of the tubing lead for the new solution to be confirmed. The user can then scan the source container bar code for the solution attached to the tubing lead that is scanned. The lot number and expiration date bar codes can also be scanned. The user can then select the "confirm" button to complete this step.

Figure 34:
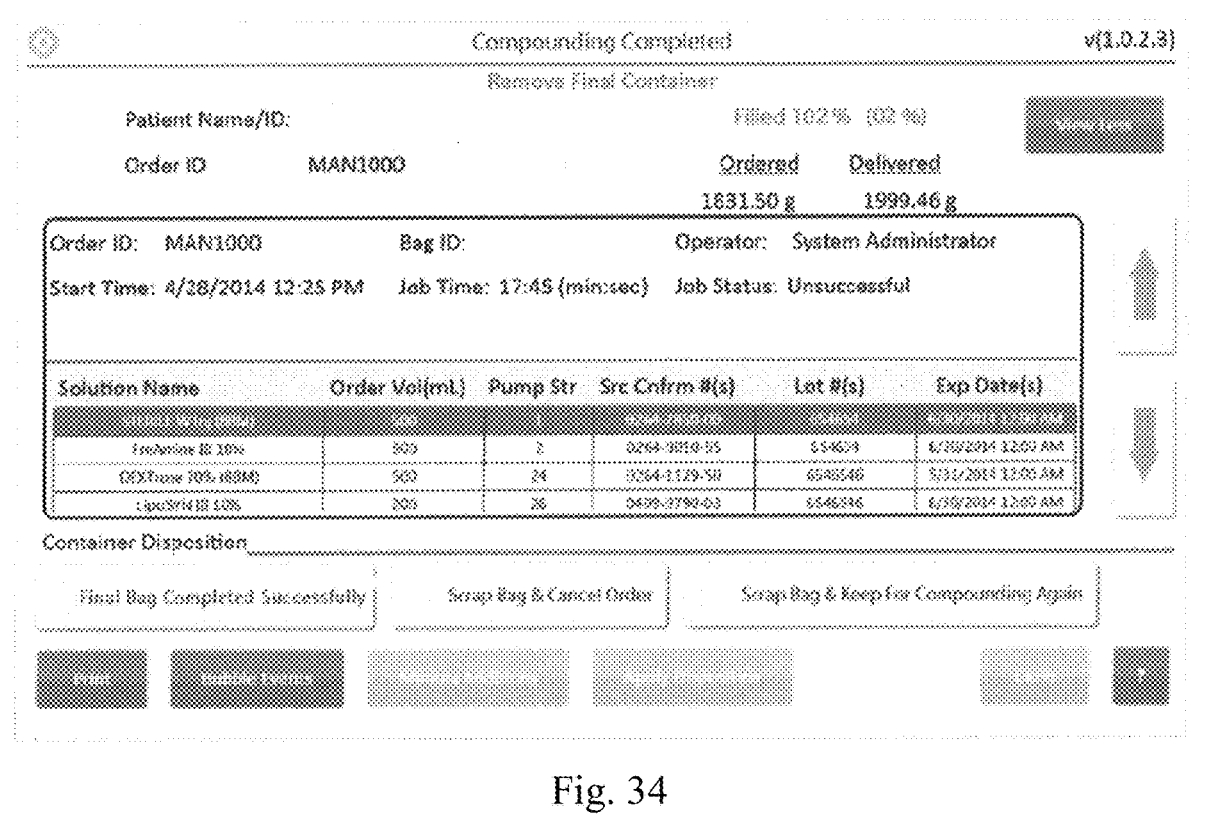

The user can then resume compounding via the interface of FIG. 34. Once the order is complete, the user can select the appropriate disposition for the receiving bag 80 (i.e., complete filling; scrap bag, etc.). Finally, the user can select the "apply disposition button." This completes the compounding process and the receiving bag 80 is ready for removal and can be used with a patient or other end user.

After all the required ingredients have been processed, the controller 2900 will direct the compounder to use a universal ingredient (UI) to flush all of the ingredients out of the manifold 20 and output tubing and into final container (e.g., fluid bag 80).

The fluid bag 80 resides on a gravimetric scale 71 that provides a final weight check back to the controller 2900 to verify that all compounded solutions were added. However, if a manual add of a particular component is necessary or desired during operation, the final check by the controller 2900 can be overridden. The load cell 71 can also be used to accomplish pump calibrations as well as in process calibrations, if desired.

The controller 2900 can include hardware or software that performs calibration of the load cell 71 and pump 40. For example, the system can be configured to allow up to 6 verification weights to ensure the load cell is within required accuracy. Pump calibration and in process calibrations ensure accuracy over the life of the disposable manifold 20.

The controller 2900 can also include a tube wear algorithm such that tubing wear is accounted for during the life of the manifold 20. In other words, the timing and speed of both the valves and the pump motors can be changed over time to account for tubing wear such that a substantially equal volume and flow rate can be achieved by the device.

The controller 2900 can also include software and/or hardware to track and possibly mark bags such that manual adds can be added to a particular bag after automatic compounding. Use of a separate (possibly networked) control panel at a manual add station will open the compounding event and allow the user to manually add ingredients while tracking the fact that such ingredients were added before approving the bag for distribution to a patient or other user.

An algorithm can be incorporated into the software and/or hardware of the controller 2900 to determine if any bubble event requires the pump 40 to stop and for the user to verify if they accept the bubble that was sensed. A flow algorithm can also be incorporated in coordination with the use of pressure sensors to detect occlusions and/or flow pressures. Furthermore, it is conceivable that intelligent bubble handling technology can be incorporated into either the controller 2900 or the occlusion or bubble sensor(s) 33o, 33s, 33o/b that monitors what has been delivered into the common volume (and attempts to determine a worse case bubble event). The technology can include hardware and/or software that causes the system to stop and require a user to accept or reject the operation depending on the presence (or lack thereof) of bubbles or an occlusion, etc. Software and/or hardware can also be provided that determines whether any occlusion or bubble event, when weighed against the size/volume of delivery, was large enough to effect accuracy, and provide a user with an automated or user defined option to accept or reject delivery of the end product.

The interface for the controller 2900 can include dual display of stations that uses colors and/or numbers to identify each station. The screen for the controller 2900 can include a first column that represents flex lines, a second and third column that represent micro lines, and a fourth or last column that represents macro lines. The screen can group the different (in this case, three) types of stations in order to present a clear picture of what fluids are at what station and what type of station it is. Of course, the number and arrangement of micro, macro and flex lines can change depending on a particular application for a different embodiment of the compounding system 1.

The controller 2900 can also be configured to require a username/password or bar coded badges to sign in/out. In addition, access can be further controlled to require username/password or bar coded badges for confirmation of required steps (e.g., addition of an ingredient that requires a prescription or that is in another way regulated).

The controller 2900 can also be configured to display a real time status of the compounding event. For example, the controller 2900 can display which solution(s) are currently being pumped from which station as well as how much solution is left in each source container 4a, b.

Templates can also be stored in the controller 2900 to quickly and efficiently determine the set-up and sequence of ingredients for a particular application or a particular patient or user. A database located in or accessible by the controller 2900 can include data related to storage, additions, removals of all drugs allowed for compounding and their associated data. The controller 2900 can be configured to include multiple interfaces for the user and can be networked such that a plurality of compounding devices can be controlled and/or monitored by a separate entity or controller. In addition, a print wizard can be incorporated into the controller 2900 software and/or hardware that automatically prints certain items when certain actions take place using the compounding device.

While certain embodiments of the invention are described above, it should be understood that the invention can be embodied and configured in many different ways without departing from the spirit and scope of the invention.

In another alternate exemplary embodiment, the occlusion sensor and bubble sensor can be positioned under the manifold common volume instead of being located in the manifold outlet tubing. Although locating the sensor area in the common volume in the manifold may make the flushing act slightly more difficult, the location of the bubble sensor in the common volume can allow a user to better discriminate which source line generated the bubble. For example, an array of bubble sensors could be located along the length of a common volume in the manifold to accomplish this feature.

In yet another exemplary embodiment, the filler 200 could be removed from the micro common volume (e.g., first channel 24*a*) and the inner diameter of the common volume could be reduced as compared to the volume depicted in, for example, FIG. 6B. This modification comes with certain complications in that manufacturing and design of the valves would be more complicated to affect the volumetric flow rates desired in the modified first channel 24*a* of the compounding device.

In another embodiment, the filler 200 could be configured with vanes on its outer diameter (OD) surface that induce turbulence and/or swirl to promote better flushing. Additionally, the filler 200 could be removable from the channel in order to provide an alternate flushing port. Likewise, the filler 200 could be removable such that different style fillers (e.g., fillers having different cross-sectional shapes, sizes, number and shape of vanes, etc.) could be used in the manifold 20.

In yet another embodiment, a cross connect channel can be located between the downstream end of the micro and macro common volumes (e.g., the first channel 24*a* and second channel 24*b*). A valve could be provided to close this channel, allowing dispensing to occur as usual, and then the valve could be opened to allow the micro common volume to be flushed by the macro pump, which operates at higher flowrates and provide more efficient flushing.

As described above, the platen/lock arm design has springs in the lock arms that press the platens against the rotors 41, 42 when the lock arms 44*a, b* are closed. An alternate approach would locate torsional springs at the platen hinge points (potentially inside the instrument) such that the platens are always spring loaded against the rotors. The platen lock arms 44*a, b* could be replaced by "platen disengagement arms" configured to pull the platens 43*a, b* away from the rotors 41, 42 during transfer set installation and removal.

The pump output is a function of upstream suction pressure. To provide better volumetric accuracy, the occlusion sensor could be used to compensate for variations in upstream suction pressure and prevent alarms due to partial occlusions. In this approach, the number of commanded pump rotations and rotor speed could be adjusted based on the measured suction pressure during pumping.

In yet another embodiment, LEDs or other types of lights or light sources can be located in the top surface of the pump under each ingredient source line. The molded manifold would guide light into the source tubing line, possibly all the way up to the spike where a visual indication could be provided if a source container or line needs attention. The light or light source would be connected to the electronic control unit for the compounding device, which would dictate when and how to provide light to a particular location, depending on error codes, programming desires, reminder notices, etc.

While it has been disclosed that a plurality of different sizes and shapes of tubings/lines and containers can be connected to the compounding device, in yet another alternative configuration of the disclosed subject matter, the compounding device can be configured for use with only a single type of container and tubing, such as only macro lines and macro containers, or only micro lines and micro containers. In this manner, the compounding device can be an effective replacement for current compounding systems and applications that include only single types of containers and lines.

The number of channels can also vary and remain within the scope of the presently disclosed subject matter. For example, three, four or more different sized channels could be incorporated into the manifold. Similarly, more than one same shaped and sized channel could be included in the manifold 20.

The strain relief clip 33 is disclosed as being pre-assembled to the lines 2011 and 2021. However, it should be understood that the strain relief clip 33 or similar structure could be attached during use or installation of the manifold. Moreover, the strain relief clip 33 could be attached only when its function is needed for a particular application. Similarly, the strain relief clip 33 can be configured in various different shapes and sizes and attached at different locations on the line or tubing. The strain relief clip 33 could also be configured as a two piece structure that can be attached at different locations on a respective one of the lines. It is also contemplated that the strain relief clip 33 can be integrated into the bubble occlusion sensor or vice versa. In addition, the strain relief clip 33 can be configured as a dampening material, adhesive or putty that can be located at a portion of the line(s) and attached to the housing to dampen movement of the lines where strain would otherwise be present.

The pump cover door could be mechanically interlocked with a specific position of platen locks (for example, a user can be prevented from closing the door if both platens are not locked into place). A lip can be provided on a lower portion of the platen to ensure that the user does not mislead a pumping segment of the tubing line to a position that is too low and that would possibly be captured between the platen and the base of the rotor (instead of being correctly placed on the roller).

The many variations and alternate structures described herein are contemplated for use in all various combinations and permutations with each other, and without certain features or components (for example, the filler can be provided without vanes 202, and the micro channel can be provided without flex ports 20*bf,* etc.)

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A valve for use in a compounding device, comprising:
a valve housing;
a valve structure located within the valve housing and configured to permit fluid to flow through the valve when in an open position, the valve structure being rotatable about a rotational axis and with respect to the valve housing,
the valve structure includes a gravity wall wherein when the valve structure is in the open position, fluid moving through the valve structure moves upward against a force of gravity after travelling through the valve and traversing the gravity wall; and an actuator configured to connect to a lower portion of the valve structure and to rotate the valve structure about the rotational axis between the open position and a closed position, wherein the actuator is configured to over rotate the lower portion of the valve structure beyond one of the open position and the closed position, and then return the lower portion to a respective one of the open position and the closed position during a respective one of an opening operation and closing operation of the valve structure.

2. The valve of claim 1, wherein the lower portion of the valve structure includes a keyway located therein.

3. The valve of claim 2, wherein
the actuator is configured to mate with the keyway in the lower portion of the valve structure and to rotate the valve structure about the rotational axis between the open position and the closed position.

4. The valve of claim 3, wherein the actuator includes a stepper motor.

5. The valve of claim 1, further comprising:
a second valve structure located within the valve housing and configured to permit fluid to flow through the valve when the second valve structure is in a second valve structure open position, the second valve structure being rotatable about a second rotational axis and with respect to the valve housing.

6. The valve of claim 5, wherein the second valve structure is different in size than the valve structure.

7. The valve of claim 5, wherein the valve housing includes a plurality of openings configured to each seat a respective one of the valve structure and second valve structure.

8. The valve of claim 1, wherein the actuator is configured to rotate the valve structure such that during actuation of the actuator a lower surface of the valve structure located adjacent the actuator rotates at a first rate of speed and an upper portion of the valve structure located further from the actuator than the lower surface simultaneously rotates at a second rate of speed that is different from the first rate of speed during actuation of the actuator due to a flexibility characteristic of the valve structure.

9. The valve of claim 1, wherein the valve structure includes an input aperture located at a top of the valve structure and configured such that fluid entering the valve structure flows along a downward fluid path and along the rotational axis of the valve structure;
an exit aperture defined in a peripheral side wall of the valve structure and configured such that fluid exiting the valve structure flows along an exit path that is substantially perpendicular to the rotational axis of the valve structure; and
the gravity wall is located within the valve structure and configured such that fluid travelling through the valve travels along the downward fluid path at an upstream side of the gravity wall, and travels on an upward fluid path on a downstream side of the gravity wall, wherein the upstream side and downstream side of the gravity wall are opposed to each other, and a direction of the downward fluid path is generally opposed to a direction of the upward fluid path, and wherein when the valve structure is in the open position, fluid moving through the valve structure moves upward against the force of gravity when travelling through the valve and traversing the gravity wall.

10. A valve for use with a compounding device, the compounding device including a compounder housing having a top surface and a bottom surface, the top surface configured to connect to the valve and to a plurality of pump devices, the valve comprising:

a valve housing having a bottom surface configured to be connected to the top surface of the compounder housing, the valve housing including a top surface configured to be spaced away from the top surface of the compounder housing when the valve housing is connected to the compounder housing;

a plurality of valve structures located within the valve housing and configured to permit fluid to flow through the valve when a respective one of the valve structures is in an open position, each of the valve structures being rotatable about a rotational axis and with respect to the valve housing, each rotational axis being substantially perpendicular to the top surface of the valve housing and to the top surface of the compounder housing when the valve housing is connected to the compounder housing;

each of the plurality of valve structures includes a gravity wall wherein, when the respective one of the valve structures is in the open position, fluid moving through the respective one of the valve structures moves upward against a force of gravity when travelling through the valve.

11. The valve of claim 10, wherein the plurality of valve structures are made from a first material having a first flexibility characteristic, and the valve housing is made from a second material having a second flexibility characteristic, and the first flexibility characteristic being greater than the second flexibility characteristic, wherein the valve structures are more flexible than the valve housing.

12. The valve of claim 10, wherein a first valve structure of the plurality of valve structures is larger in size as compared to a second valve structure of the plurality of valve structures.

13. The valve of claim 10, wherein the bottom surface of the valve housing is parallel with the top surface of the valve housing and configured to be substantially parallel with the top surface of the compounder housing.

14. A method for operating a valve in a compounding device, comprising:

providing a valve housing;

providing a valve structure located within the valve housing and configured to permit fluid to flow through the valve when the valve structure is in an open position, the valve structure being rotatable about a rotational axis and with respect to the valve housing, the valve structure including a gravity wall wherein, when the valve structure is in the open position, fluid moving through the valve structure moves upward against a force of gravity after travelling through the valve and traversing the gravity wall;

rotating a lower portion of the valve structure to cause the lower portion of the valve structure to rotate at a first speed and an upper portion of the valve structure to rotate at a second speed different from the first speed.

15. The method for operating a valve of claim 14, wherein rotating includes rotating the valve structure between the open position and a closed position, and further includes over rotating the lower surface of the valve housing beyond one of the open position and closed position, and then returning the lower surface to the one of the open position and closed position.

16. The method for operating a valve of claim 14, further comprising:

providing a compounder housing.

17. The method for operating a valve of claim 14, wherein rotating includes rotating the valve structure to the open position such that a lower surface of the valve structure arrives at the open position before an upper portion of the valve structure arrives at the open position.

18. The method for operating a valve of claim 17, wherein rotating includes rotating the valve structure to the open position such that the lower surface of the valve structure arrives at the open position by travelling in a direction reverse to a direction of travel of the upper portion of the valve structure.

\* \* \* \* \*